(12) United States Patent
LaFreniere

(10) Patent No.: US 12,414,687 B2
(45) Date of Patent: Sep. 16, 2025

(54) HEADSET SYSTEM FOR BIOMEDICAL IMAGING FOR EARLY TUMOR DETECTION

(71) Applicant: Zakariah LaFreniere, Miami, FL (US)

(72) Inventor: Zakariah LaFreniere, Miami, FL (US)

( * ) Notice: Subject to any disclaimer, the term of this patent is extended or adjusted under 35 U.S.C. 154(b) by 377 days.

(21) Appl. No.: 17/946,990

(22) Filed: Sep. 16, 2022

(65) Prior Publication Data

US 2023/0086228 A1    Mar. 23, 2023

Related U.S. Application Data

(60) Provisional application No. 63/247,153, filed on Sep. 22, 2021.

(51) Int. Cl.
*A61B 3/00* (2006.01)
*A61B 3/14* (2006.01)
(Continued)

(52) U.S. Cl.
CPC ............... *A61B 3/005* (2013.01); *A61B 3/14* (2013.01); *G06T 7/0012* (2013.01);
(Continued)

(58) Field of Classification Search
CPC ..... A61B 3/005; A61B 3/14; A61B 2090/502; A61B 3/0025; A61B 3/1216; A61B 3/145;
(Continued)

(56) References Cited

U.S. PATENT DOCUMENTS 9,357,920 B2   6/2016  Yates et al.
10,039,445 B1* 8/2018  Torch ...................... A61B 5/18
(Continued)

FOREIGN PATENT DOCUMENTS

CN   105426695     8/2018
CN   110022753 B   2/2022
(Continued)

OTHER PUBLICATIONS

Grand Medicine © Sclerology Signs and Markings.

*Primary Examiner* — Bo Joseph Peng
(74) *Attorney, Agent, or Firm* — Tom Ciesco; MENLO PARK PATENTS

(57) ABSTRACT

An independent wearable biomedical imaging system for early tumor detection the system including a physician headset having a graphical display in wireless communication with a patient headset having a left and right camera. The physician headset includes a map template database disposed in the memory storage drive including data specifying anatomical location of a patient tumor using sclera scans of a patient sclera and iris received from the patient headset. The physician can visually access the sclera scans from the patient headset camera and overlay with the map template to compare patient scan biomarkers with the map data. The physician may use the results in indicating strong genotype predisposition to tumors and tumor formation. The system algorithm would continue to amass biodata in the datasets helping the physician to increase accuracy in generating eye reports and statistical probability of tumor as well as genetic marker predisposition of the same.

20 Claims, 15 Drawing Sheets

(51) Int. Cl.
*G06T 7/00* (2017.01)
*G06V 40/18* (2022.01)
*G16H 40/63* (2018.01)
*A61B 90/50* (2016.01)

(52) U.S. Cl.
CPC ........... *G06V 40/193* (2022.01); *G16H 40/63* (2018.01); *A61B 2090/502* (2016.02); *G06T 2207/20081* (2013.01); *G06T 2207/30041* (2013.01); *G06T 2207/30096* (2013.01); *G06V 2201/031* (2022.01)

(58) Field of Classification Search
CPC ............ A61B 2090/365; G06T 7/0012; G06T 2207/20081; G06T 2207/30041; G06T 2207/30096; G06V 40/193; G06V 2201/031; G06V 2201/03; G16H 40/63; G16H 30/20; G16H 50/20; G16H 30/40
See application file for complete search history.

(56) References Cited

U.S. PATENT DOCUMENTS

| | | | |
|---|---|---|---|
| 10,178,948 B2 | 1/2019 | Lin et al. | |
| 11,129,532 B2 | 9/2021 | Fletcher et al. | |
| 2015/0324974 A1 | 11/2015 | Garber et al. | |
| 2016/0270656 A1* | 9/2016 | Samec | A61B 3/113 |
| 2017/0115742 A1* | 4/2017 | Xing | G06F 3/0485 |
| 2022/0133212 A1* | 5/2022 | Krueger | A61B 3/0041 600/301 |

FOREIGN PATENT DOCUMENTS

| | | |
|---|---|---|
| KR | 101197678 | 11/2012 |
| KR | 102112268 B1 | 5/2020 |
| RU | 40704 U1 | 9/2004 |
| RU | 2236164 C1 | 9/2004 |
| RU | 48147 U1 | 9/2005 |

* cited by examiner

HEADSET SYSTEM FOR BIOMEDICAL IMAGING FOR EARLY TUMOR DETECTION

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

Trademarks used in the disclosure of the invention, and the applicants, make no claim to any trademarks referenced.

CROSS-REFERENCE TO RELATED APPLICATIONS

"This application claims the benefit of U.S. Provisional Patent Application No. 63/247,153 filed on Sep. 22, 2021, which is incorporated by reference herein in its entirety."

BACKGROUND OF THE INVENTION

1. Field of the Invention

The invention relates generally to the field of wearable technology; specifically, the invention is a dichotomous wearable headset system engineered to enable chiropractors, naturopathic doctors, and medical doctors, to non-invasively screen patient organs and glands for evidence of genetic predisposition to tumors, and also subclinical neoplasms, by applying the sciences of Physical Iridology and Sclerology.

2. Description of Related Art

Currently, allopathic methods for early cancer detection offer no reliable non-invasive means of early malignant tumor detection. The most sensitive two-million-dollar biomedical imaging machines such as the Positron Emission Tomography (PET) scans have a lower limit of sensitivity, and can only detect a malignant tumor at 0.5 cm or larger. That leaves a wide coverage gap for early malignant tumor detection where during this critical period of surveillance, due to inherent limitations of current biomedical imaging technology, oncologists are unable to detect malignant tumors until later stages, and where patient cancer survival rates plummet. The most common cancer in American women is breast cancer. Present attempts to mitigate breast cancer mortality using mammograms are invasive and unreliable. Here, the woman is required to regularly schedule in-person visits with her physician, participate in having each mammary gland pinched in a vice of up to forty pounds of pressure per square inch, as well as suffer exposure to mutagenic ionizing radiation. The cons with this allopathic conventional cancer screening methodology are obvious. First, the intense pressure of up to forty pounds psi on each mammary gland, typically causes rupture of a cyst or other growth, and could possibly have the disastrous effect of breaking a malignant tumor, and causing malignant cancer cells to spread system-wide in the body via the bloodstream. As if this were not enough, the regularly scheduled visits for the mammogram entails constant exposure of breast tissue to ionizing radiation which over time could trigger cell mutations and induce gene expression for cancer. Paradoxically, the very breast cancer early screening modality that is supposed to early detect a malignant tumor, could end up causing it to metastasize by the forty pounds of pressure psi applied to each breast, or otherwise induce new cancers from ionizing radiation exposure. Another issue with breast cancer screening is the high rate of false positive diagnosis. It is not uncommon for small malignant tumors to be missed by the oncologist where the clinician has inexperience reading images, or where the dense breast tissue of the patient conceals the malignant tumor from view. As for men, the top cancer in American males is prostate cancer. For three decades the Prostate Specific Antigen (PSA) test has been the gold-standard for screening men for cancer of the prostate gland. Notwithstanding the fact that the PSA test is invasive, requiring the patient to suffer painful needle sticks, the PSA test is prone to error, and contributes greatly to false positive cancer diagnosis. This in turn unnecessarily exacerbates the cost of health care as patients are pressured into unnecessary (and painful) needle biopsies of the prostate gland, and other unnecessary surgical procedures.

In 1971, President Richard Nixon declared "war on cancer" upon signing the National Cancer Act (NCA) into law. Back in 1971, cancer was the #1 killer of Americans. Despite billions in tax revenue appropriations earmarked for cancer research—sadly, fifty years later, cancer has dropped only one place, and is now the #2 killer of Americans behind heart disease. According to the World Health Organization (WHO), the United States of America ranks 4/195 nations in worldwide cancer mortality. In 2021, 608,570 Americans died from cancer. Oncologists report that they are often unable to detect cancer until later stages, where survival rates plummet. The issue is early cancer detection. Based on the present state of conventional biomedical imaging technologies, and the fact that cancer mortality rates in the U.S. have remained unchanged largely for the past half century, the instant innovation promises to help the U.S. win President Nixon's fifty year "war on cancer." That said, Zakartek Solutions, LLC, a newly formed technology company based in Miami, Florida, has the panacea in the way of a new wearable biomedical imaging technology called: SCLERA-scope™.

In 2022, the state-of the-art for wearable Augmented Reality (AR) headsets dedicated to the healthcare market is in an embryonic state. In 2014, RealView Imaging, Ltd., based in the State of Israel, pioneered medical holography with a wearable technology called the Holoscope. The Holoscope enables surgeons—allopaths, the ability to project 2d images of patient anatomy from conventional biomedical images (e.g. CT scans, MRI, etc.) into 3d real space. While impressive, this holographic technology does not address the present need for a new AR headset to non-invasively early detect malignant tumors. The Microsoft Corporation is another company that has applied AR wearable technology in the healthcare space. The Microsoft HoloLens2 is a $3,500 wearable technology aimed at enterprise markets such as medical colleges—nil for the cancer patient. The HoloLens2 features 3d holographic functionality that can project images into real space. One application of HoloLens2 is at Case Western Reserve University to enhance medical student pedagogy in labs. Another application of the HoloLens 2 is to help train surgical residents prior to actual surgery to mitigate medical mistakes. Again, as impressive as the HoloLens2 AR headset is, it is aimed at the enterprise market, and fails to address the exigent public health crisis of cancer mortality in the U.S. Ironically, even though Apple, Inc. co-founder Steve Jobs died in 2011 from complications related to pancreatic cancer, the present management at Apple Inc., has failed to introduce any AR wearable technology for early cancer detection in the decade since the death of Steve Jobs. Sadly, rather than pioneer in the medical space to fight cancer, Apple Inc., has opted instead to enter its AR wearable technology in the already crowded AR/VR headset segment (e.g. Oculus Rift, HTC Vive, Quest 2, PlayStation VR, etc.) Vestibular First has a wearable headset for patients called Insight Pro Infra Red Video Goggles; however, the Insight Pro technology is engineered for patients suffering from vertigo. The most recent WHO statistics do not list "vertigo" as being among the top killers of Americans. The Insight Pro Infra Red Video Goggles do nothing to mitigate the more than 608,000 Americans who die per annum from malignant tumors. The medical specialty of ophthalmology has introduced an AR wearable headset called Hem; however, this is again allopathic medicine, and such AR technology is used only to detect diseases of the eye: glaucoma, diabetic retinopathy, etc. While the Hem may be able to detect brain tumors by examining the fundus (rear) of the patient eye, it is not seeking early-stage cancer prevention nor preventive care; this is the domain of naturopathy. Ophthalmology is instead concerned with palliative care, which means that once the Hem locates eye pathology, they will not concern themselves with the root cause, but rather treat the symptoms of the underlying pathology with drugs and/or surgery. This is reactive medicine.

On the naturopathic preventive medicine side, the present state-of-the-art with respect to AR wearable technology, AI/ML, and holographic functionality is scant. The majority of the cutting-edge innovation in Iridodiagnosis stems from a handful of nations—namely, Russia, China, and South Korea. With respect to the present innovation, the material relevant prior art emanates from an inventor from the State of Israel. The named inventor is an Iridologist and author Dr. Miriam Garber who is the Founder & CEO of Eye-CU Life Systems, Ltd., based in the State of Israel. Dr. Garber's patent is for an invention called "computerized iridodiagnosis" (US 2015/0324974 A1) and has been assigned to her company. The current status of this utility patent shows "abandoned" since 2015 for "failure to respond to patent examiner office action." A more recent prior art search reveals that as of Sep. 15, 2022 this patent is "withdrawn." The "novel and nonobvious" element of the instant innovation over the Dr. Garber "computerized iridodiagnosis" innovation, as well as the foreign prior art from Russia, China, and South Korea, is that it moves forward, beyond primary reliance upon just Physical Iridology science alone, and instead places the majority of the onus for "earliest possible detection of tissue level disease" (in this case cancer) on the latest developments in Sclerology science— hence the name of the instant innovation: SCLERAscope™.

According to the late Dr. Bernard Jensen, the human iris that comprises the colored portion of the anterior segment of the human eye, is an extension of the central nervous system. With respect to human anatomy and physiology, the human iris contains hundreds of thousands of nerve endings (autonomic, middle, and sensory), capillaries, and muscle fibers; therefore, the iris has a *nexus* to every organ and gland in the body. Since the iris is part of the brain and nervous system, it serves as a direct diagnostic indicator of systemic health. While the human iris is said to be "fixed" at birth, and does not change after the first eighteen months outside of the womb, subsequent symptoms of pathology appear in the iris as markers. In the science of Physical Iridology, or Iridodiagnosis (also Irisology), the focus of the trained Iridologist and naturopath is on changes in the iris to Dx the disease state of the associated tissue, and discern nutritional deficiencies to provide the right Rx. The iris is the most complex fibrous membrane structure in our body and is connected to the cerebrum and parts of the body through nerves. The physical and chemical changes that occur in each organ or gland, histologically, are reflected in the patient irides. In one sense, the eyes are indeed the "window to the soul." This patient biodata is transmitted along nerve pathways and reflect change in the shape of the fibrous tissue by unique markings and colorings. The expert analysis of the color and structural changes in the iris image shows the health status of the body organs, the degree of accumulated toxins (e.g. prescription drugs) and environmental toxins from some municipal water sources, polluted air from noxious automobile tailpipe emissions, second hand cigarette smoke, etc. Peer reviewed articles from nations around the globe like South Korea, Russia, and China, establish Iridodiagnosis as being a robust science-based non-invasive health assessment modality. Out of all foreign nations that embrace Iridodiagnosis—China, India, Russia, South Korea, Germany and Japan, Russia stands apart by mandating that any practitioner of Iridology first earn a medical degree.

Mankind has been designed by the Creator as a bilateral species: two hemispheres of the brain for cognition, two eyes for sight, two nostrils and lungs for respiration, two ears for audio and balance, two kidneys for serum filtration of drugs and waste, two adrenals for metabolism and immune function, two legs for balance and ambulatory mobility, etc. Accordingly, the iris map denoting the physical location of the organs and glands corresponds to this bilateral anatomical system. For example, the pattern of the left iris is reflected by the organs and members located on the left side of the body. The pattern of the right iris is reflected by the organs and members located on the right side of the body. So, the left kidney and adrenal gland is reflected in the left iris, and the right kidney and adrenal gland is reflected in the right iris. On the other hand, the organs that exist only on the left side of the body (spleen) appear only in the left iris, and the organs that exist only on the right side (gall bladder) only appear in the right iris. Organs or glands (liver) appearing in the center of the body appear in both irides. The iris is tightly connected to the nervous and circulatory systems and directly to the sympathetic nervous system, so it is sensitive to internal body stress and inflammation down to the tissue level. For example, if a toxic substance enters the body (e.g. vaccine), the color of the iris may change showing tissue level pathology. Thus, observing the irises reveals the person's natural constitution, health status, presence, and extent of inflammation, drug accumulation, acidity, and healing process.

As the name implies, the instant innovation SCLERAscope™ represents a "novel and non-obvious" advance or improvement of related art which heretofore has relied mainly upon the iris or Iridodiagnosis. This innovation happens mainly by advancing the science away from solely screening the iris, and placing the majority of the diagnostic emphasis instead on the sclera or sclera analysis. While the iris data is not wholly ignored in the present innovation, it plays a minor role in Sclerology. For example, the known gold-standard tumor biomarkers in this application for iris is seven, while the tumor biomarkers for sclera total thirteen (N12+D5) meaning there is double the amount of tumor biodata available in the sclera versus the irides. Perhaps the greatest pioneer in the science of Sclerology is American retired naturopath Dr. Mehlmauer of Grand Medicine in California. Dr. Mehlmauer has stated with respect to iris versus sclera: "As important as the iris is as a non-invasive health assessment tool, the sclera can show so much more.

Indeed, sclera markings can reveal evidence of early tumor formation in the organs and glands years before symptoms."

BRIEF SUMMARY OF THE INVENTION

Accordingly, a primary utility of the innovation that relies mainly upon the science of Sclerology, is to help chiropractors, naturopathic doctors, and medical doctors, non-invasively screen patients for early-stage malignant tumors. The name of the new wearable biomedical imaging technology described in this utility patent application is: SCLERAscope™. Only reference to the wearable biomedical imaging technology or headset will be made from here on out. The term wearable biomedical imaging technology may be substituted for the term headset in the description herein.

The routine sclera exam as part of active surveillance for cancer screening using the wearable technology innovation between the physician certified in Physical Iridology and Sclerology science, and the patient, is about ten minutes. In harmony with recent trends towards tele-health, the remote sclera screening using the wearable headset can be performed from the comfort of the patient's home, or at the physician's home office. The sclera exam does not require in person visits to the doctor office, that may require requesting time off from work, ruined days off, lengthy doctor office visits waiting in long queues, etc. The physician starts the sclera exam by donning their headset. Both the patient headset and physician headset feature secured biometric iris scan access. The utility here being to ensure confidentiality of patient medical records under statutory regulations like the Health Insurance Portability and Accountability Act (HIPAA). The headset is engineered to operate untethered to any desktop computer or PC, laptop, tablet, etc. So long as each headset is fully charged and is powered on, the physician can complete an entire sclera exam including accessing patient medical records using the headset and manipulate the user interface with a standard wireless mouse and wireless keyboard. The physician may also complete the sclera exam with any patient over any geographical distance so long as both headsets are fully charged and powered on. The digital photos used for sclera exam are high resolution digital photos of the anterior segment of the patient eye, obtained from a bilateral digital camera system housed in the patient headset. Typically, the Sclerologist is ideally going to want about twelve quality pictures of each eye (pupil, iris, and sclera). This patient digital biodata will be securely stored in a secure location, such as the cloud. Unlike the ophthalmologist allopathic medical doctor, who is looking to the fundus or rear of the patient eye, to glean information about diseases of the eye such as glaucoma and diabetic retinopathy, the naturopath, chiropractor, and preventive medicine physician is using the wearable technology to assess the anterior segment of the patient eye: pupil border dynamics, irides, and sclerae. Rather than looking for diseases of the eye, the Sclerolgist instead focuses on locating evidence of tissue level pathology in the organs and glands—namely, congestion, inflammation, stress, and early-stage malignant tumors. The physician headset and patient headset system have many useful features. For example, both feature wireless charging having utility in that neither poses a tripping hazard from a labyrinth of cords and wires emanating from the headset. There is audio functionality by wireless communication having utility by allowing the doctor and patient team to dialogue during the sclera exam. In some embodiments, the physician headset features 3d holographic tomography of patient organs and glands in real space. Medical holography has utility in the higher education space where the wearable headset could be applied to enrich medical student pedagogy at Harvard Medical School, Parker Chiropractic College, or Bastyr University College of Naturopathic Medicine. The utility being to improve medical training of the next generation of chiropractors, naturopathic doctors, and medical doctors in Physical Iridology and Sclerology science. Also, for better educating practicing physicians interested in obtaining certification in exchange for continuing education (CE) credit. Another feature of the innovation is AI/ML functionality. A dedicated supervised learning algorithm will enable the physician headset to receive labelled datasets based upon the gold-standard tumor biomarkers established by researchers at Grand Medicine. The algorithm will be trained on vetted gold-standard tumor biomarkers, at present twenty-two, between the pupil (2), iris (7), and sclera (13). The algorithm will then feature recognize and feature extract the relevant patient tumor biomarkers from each sclera exam. Based on the success of supervised algorithms created by other companies like the I.B.M. Watson, and Google's Alpha Go, the trend in technology shows that AI/ML functionality has utility in healthcare by helping mitigate human errata, in this case medical misdiagnosis for cancer as false positives and false negatives. The two headsets will feature a state-of-the-art cooling system to ensure each headset does not overheat and cause damage to the internal electronics, and also discomfort for the user.

The patient headset will be a far simpler engineering design when juxtaposed to the physician headset. The patient headset for early cancer detection will nonetheless offer an array of features having great utility. For example, the patient headset will feature secured biometric iris scan access; this has utility in ensuring confidentiality of patient medical records. Wireless functionality is included in the patient headset, the utility here being that the absence of long power cords or wires hanging from the headset removes the danger of entanglement and no tripping hazard for the user. Graphene battery technology, or some other suitable technology known by one skilled in the art, being very useful insofar as it is not prone to overheat, explode, or catch fire like lithium-ion. The patient headset will feature "digital arches" allowing the patient to physically move the eyelids while wearing the headset to remove unwanted noise like eyelids and eyelashes from interfering with the bilateral digital camera system. The patient headset will also feature wireless charging functionality, ideally on a charging pad. The patient headset also features a state-of-the-art cooling system so that there is no overheating from use, and to ensure that the temperatures remain constant for optimal protection of the internal components and circuitry of the patient headset.

Implemented in the headset system according to the present invention is a subclinical neoplasm detection system based upon the latest cutting-edge developments in Sclerology science. The headset system technology can be comprised of an article of eyewear featuring a high-quality frame body that supports a bilateral digital camera system used to take digital images of a user's pupil, iris, and sclera. While not presently the state-of-the-art, ideally developments will one day enable the digital cameras to capture the anterior segment tumor biodata through the eyelid, without a patient having to physically lift vertically, horizontally, and laterally on their eyelids to remove noise such as patient eyelashes, eyelids, etc. The digital images may be subsequently analyzed by a doctor trained in Physical Iridology and Sclerology, for evidence of malignant tumors.

The early tumor detection functionality of the innovation is based largely upon the histopathological N12 and D5 tumor biomarkers (N=neoplasm and D=Drug) discovered by Dr. Mehlmauer at Grand Medicine. The genius of this histologically based cancer screening approach, is that it enables chiropractors, naturopathic doctors, and medical doctors, a reliable, cost-effective, and non-invasive biomedical imaging tool, to better screen patients for malignant tumors. The present innovation having utility in that it cannot be associated with any of the present cons of invasive cancer patient screening. For example, in breast cancer malignant tumors may indeed be present at <0.5 cm which is invisible to a mammogram and PET scan. Also, there is no compression of a woman's mammary glands under twenty to forty pounds of pressure, nor is there any exposure of the breast tissue to ionizing radiation which can trigger cell mutations. In the case of men, the instant innovation is clearly superior to conventional prostate cancer screening which includes the highly error prone PSA blood test. Another utility of the innovation is that while the two aforesaid screening modalities are aimed at top two cancers impacting American women and men, the non-invasive sclera assessment is able to screen the same patient for evidence of every cancer subtype listed by the NCI: breast cancer; prostate cancer; lung cancer; thyroid cancer; colon cancer; liver cancer; sarcoma; lymphoma; pancreatic cancer; cervical cancer; cholangiocarcinoma, etc.

The headset system physician headset includes a housing made of sustainable natural material, including a headset housing having a housing shell including a nose rest, a headset plate (or visor) having a plate perimeter, the headset plate including a headset plate exterior surface and a headset plate interior surface, the headset plate being secured to the housing shell along the plate perimeter and a headset securing bracket for engaging a securing machine for donning the physician headset. The physician headset features include a power source, such as graphene battery technology, a receiving/transmission communication system for receiving and sending information to a patient headset at a remote distant location, and a CPU for processing information in the physician headset. The physician headset includes a memory storage drive, a circuit board for integrating the power source, the graphics processing system, the receiving/transmission communication system, the CPU and the memory storage drive and at least one graphical display disposed on the interior surface of the headset plate, the at least one graphical display for displaying patient pupil border dynamics, iris tumor markers, and sclera tumor biomarkers over a transparent Physical Iridology map, and Sclerology map, having utility by helping ensure the accurate placement of the tumor mark to the correct organ or gland. The physician headset includes a map template database disposed in the memory storage drive wherein the map template database includes data specifying anatomical location of a patient tumor using sclera scans of a patient sclera and iris received from the patient headset; and a headset controller panel for controlling functions carried out by the headset. The controller for the instant innovation could be in the form of a wireless mouse, wireless keyboard, or voice activation. The graphics processing system processes high-resolution image data from the patient headset and display the high-resolution image data in combination with corresponding template data for review by a physician. The qualified medical doctor, chiropractor, or naturopathic doctor, who is certified in Sclerology, may don the physician headset, to access the patient pupil, iris, and sclera scans from the patient headset, and the map template database data from the memory storage drive. Captured video information on the patient pupil, iris, and sclera, is saved in the memory storage drive; the physician may elect to use a wireless keyboard to label this patient digital biota in the software with basic minutiae like patient name, date of sclera exam, medical record number, and the particular quadrants of the eye being pictured RUQ, RLQ, RMQ, RLQ, (e.g. Right Upper Quadrant, Right Lower Quadrant, Right Medial Quadrant, Right Lateral Quadrant, etc.) The patient labeled biodata can be securely stored in the proprietary software system to ensure HIPAA compliance, and provided in a format to match with the map template system. The map template database may include both Physical Iridology and Sclerology based templates. The headset controller panel may be remote and in wireless communication with the receiving/transmission communication system. The at least one graphical display may be mounted on the circuit board. The power source may include a rechargeable battery such as graphene technology, or one not prone to overheating, explosion, or fire, one skilled in the art would know best which battery technology is superior for the purpose. The housing shell may include a charging port to charge the rechargeable battery, or functionality to charge wirelessly on a charging pad. The wearable headset system is ideally engineered to operate as a wearable computer system, and function independent of any desktop PC; however, some embodiments of the innovation may allow for cross compatibility with a PC, laptop, tablet, etc. The physician headset may include AI/ML functionality. Each patient examination will provide the doctor with the opportunity to vet the patient digital images for storage in a secured archive. This archive may be accessed by the Sclerologist to label new datasets such as newly discovered tumor biomarkers, to train the supervised learning algorithm. The learning algorithm will become more and more proficient over time feature recognizing and feature extracting histopathological evidence of cancer, or digital pathomics, and may help generate sclera reports of statistical probability output of tumor/no tumor, and differential Dx of malignant tumor/benign tumor. Another aspect of the present invention is directed to a patient headset for biomedical imaging of the anterior segment of the patient eye screening for the presence of tumor biomarkers. Specifically, this entails close examination of the patient pupil border dynamics, irises, and sclera. In Physical Iridology and Sclerology, these are the three focal areas that can provide evidence of histopathology in the patient organs and glands. The patient headset system includes a headset housing comprised of sustainable natural material having utility in not polluting the environment with non-biodegradable plastics and the like. A housing shell for the camera system and other electronic components, with sufficient "digital arches" room to insert fingers and remove unwanted noise like eyelids and eyelashes. The patient headset includes a headset plate exterior surface and a headset plate interior surface, the headset plate being secured to the housing shell along the plate perimeter. The patient headset (and physician headset) must necessarily include a robust securing bracket or "halo" to comfortably set the machine on the skull, and a bilateral digital camera system that is adjustable to each patient's eyes. The patient headset includes a patient headset power source, secured biometric iris scan, video processing system, a receiving/transmission communication system and a CPU for processing information in the headset. The patient headset includes a memory storage drive, a circuit board for integrating power source, video processing system, receiving/transmission communication system circuit, left camera, right camera, CPU and memory storage and may include a map template database disposed in the memory storage drive or in wireless communication with the patient headset. The map template database includes data specifying anatomical location of a patient tumor using sclera scans of a patient sclera and iris and has obvious utility insofar as it helps to educate the patient about the location of possible tumors in the body organs and glands. The video processing system can capture high resolution images from the left camera and the right camera and integrate with a map template system for use by a physician. Captured video information on the patient's pupil, iris, and sclera totaling about twenty total digital images per examination, is saved in the memory storage drive, labeled by the physician, stored securely in compliance with HIPAA, and provided in a format to match with the map template system. The power source may include a rechargeable battery such as graphene technology; however, one skilled in the art would know which battery technology is superior for the particular embodiment. The exterior patient headset housing shell may include a charging port to charge the rechargeable battery, whereas some embodiments would include wireless charging functionality such as via a wireless charging pad. Both the physician headset and the patient headset each feature a state-of-the-art cooling system to prolong the life of the internal circuitry, and prevent overheating and machine premature failure.

Another aspect of the present invention is directed to a method of using an independent wearable biomedical imaging system for early tumor detection using the physician headset according to claim 1, the method comprising providing the physician headset having a headset housing, having a housing shell including a nose rest, a headset plate (or visor) having a plate perimeter, the headset plate including a headset plate exterior surface and a headset plate interior surface, the headset plate being secured to the housing shell along the plate perimeter and a headset securing bracket for engaging a securing device for donning the physician headset. The physician headset includes a power source, secured biometric iris scan access system to ensure confidentiality of patient medical records, an audio system including a microphone and speakers, a graphics processing system, a wireless capable receiving/transmission communication system for receiving and sending information to a patient headset, and a CPU for processing information in the headset independent of a PC or laptop. The physician headset includes a memory storage drive, a circuit board for integrating the power source, the graphics processing system, the receiving/transmission communication system, the CPU and the memory storage drive and at least one graphical display disposed on the interior surface of the headset plate, the at least one graphical display for displaying sclera and iris scans received from a patient headset and overlayed template information. The physician headset may also include a cooling system such as a small fan system to keep the electronical components cool and prevent overheating. The physician headset includes a map template database of the pupil, iris, and sclera disposed in the memory storage drive wherein the map template database includes data specifying anatomical location in the body organs and glands of a patient tumor using sclera scans of a patient sclera and iris received from the patient headset; and a headset controller panel for controlling functions carried out by the headset. The physician headset may also include an input device such as a wireless keyboard or other such hardware. The graphics processing system processes high-resolution digital quality images from the patient headset and display the high-resolution image data in combination with corresponding template data for review by a chiropractor, naturopathic doctor, or medical doctor trained in Physical Iridology and Sclerology. The method includes providing a patient headset including a patient headset housing having "digital arches" or physical "finger slots" disposed in the patient headset housing allowing the patient to comfortably remove unwanted noise blocking the digital cameras. The patient headset includes a cavity containing a left camera, a right camera, a battery, a video processing system, a receiving/transmission circuit and a patient headset CPU for controlling the patient headset.

These and other objects, features, and advantages of the present invention will become more readily apparent from the attached drawings and the detailed description of the preferred embodiments, which follow.

BRIEF DESCRIPTION OF THE DRAWINGS

A further understanding of the nature and utility of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

Corresponding reference characters indicate corresponding parts throughout the several views. The exemplifications set out herein illustrate embodiments of the invention and such exemplifications are not to be construed as limiting the scope of the invention in any way.

DETAILED DESCRIPTION

Figure 1:
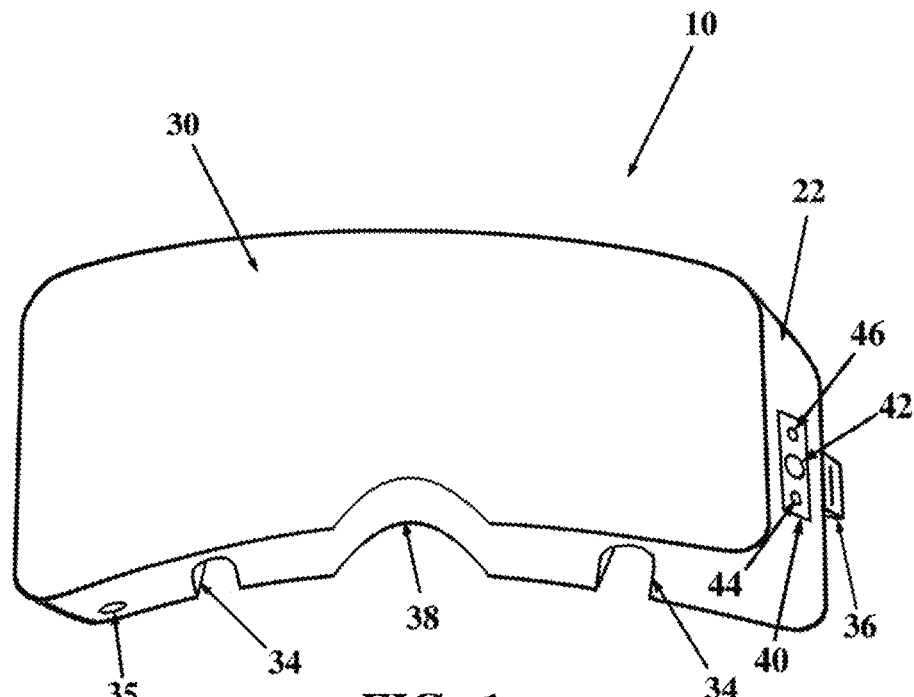
FIG. 1 is a front right bottom perspective view of the patient headset according to the present invention.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention. In the following description, for the purposes of explanation, numerous specific details are set forth in order to provide a thorough understanding of the described embodiments. It will be apparent to one skilled in the art however that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token however, no single feature or features of any described embodiment should be considered essential to every embodiment of the invention, as other embodiments of the invention may omit such features.

In this application the use of the singular includes the plural unless specifically stated otherwise and use of the terms "and" and "or" is equivalent to "and/or," also referred to as "nonexclusive or" unless otherwise indicated. Moreover, the use of the term "including," as well as other forms, such as "includes" and "included," should be considered non-exclusive. Also, terms such as "element" or "component" encompass both elements and components including one unit and elements and components that include more than one unit, unless specifically stated otherwise.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure be considered as an example of the principles of the invention and not intended to limit the invention to the specific embodiments shown and described.

The headset system according to the present invention is a dichotomous wearable biomedical imaging technology: the Physician headset and the patient headset. The goal is to allow the physician and the patient to conduct the sclera exam for routine cancer screening untethered from a PC, laptop, tablet, etc. This wireless functionality allows the doctor and the patient to enjoy an anxiety free user experience, free from worry about becoming entangled in power cords or wires hanging from the headset. In a wireless system, there are no tripping hazards for the physician, the patient, or medical staff. This attention to detail has utility in reducing product liability. It should also serve to encourage faithful usage of this form factor for active surveillance for cancer screening over the course of a lifetime. Providing there is sufficient battery charge, the wearable technology system should be able to proceed regardless of geographic distance between the two-headset system.

Figure 2:
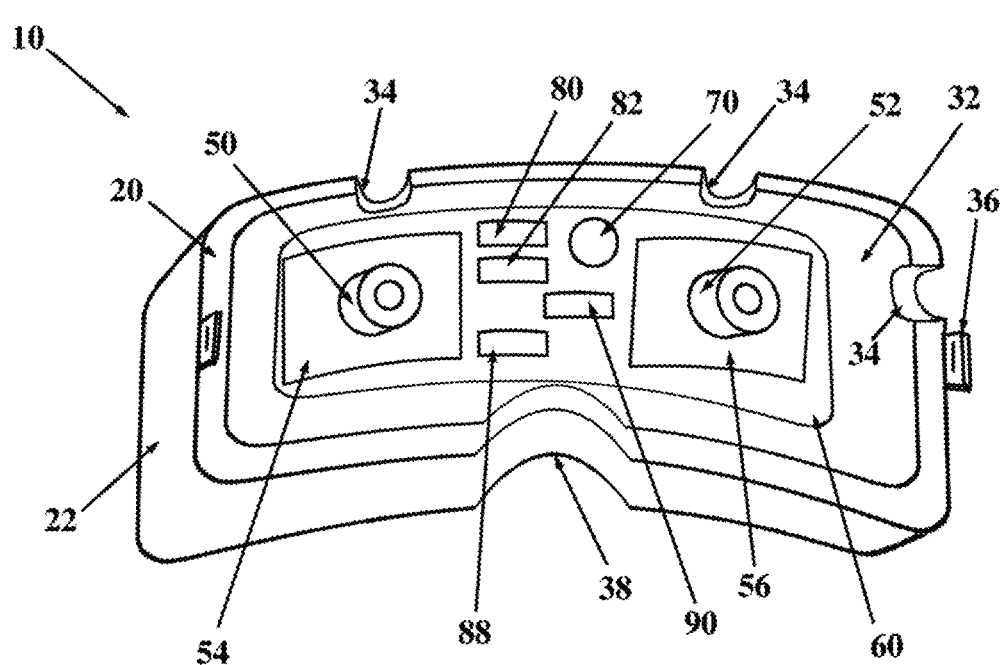
FIG. 2 is a rear left bottom perspective view of the patient headset shown in FIG. 1.
Figure 3:
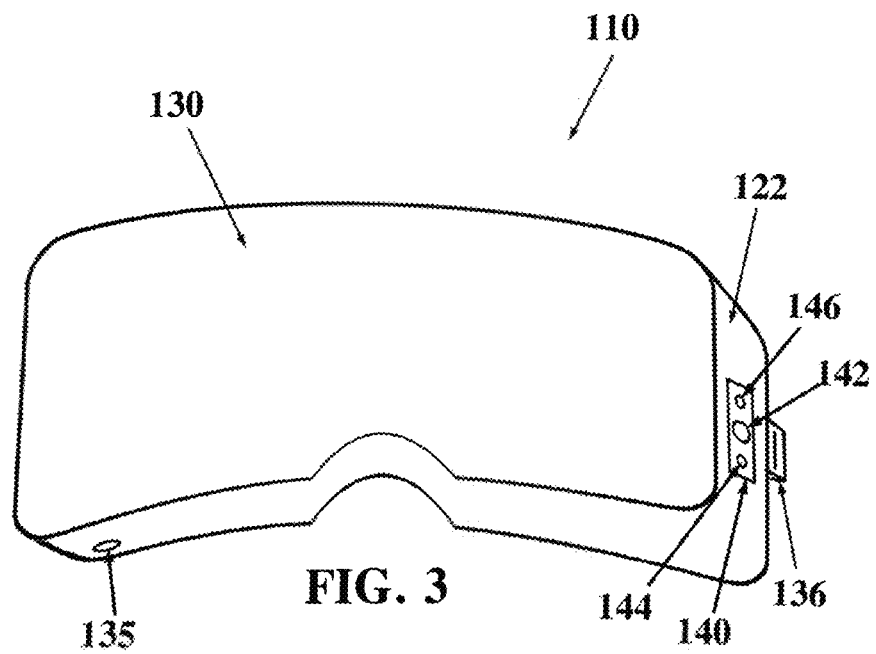
FIG. 3 is a front right bottom perspective view of the physician headset according to the present invention.
Figure 4:
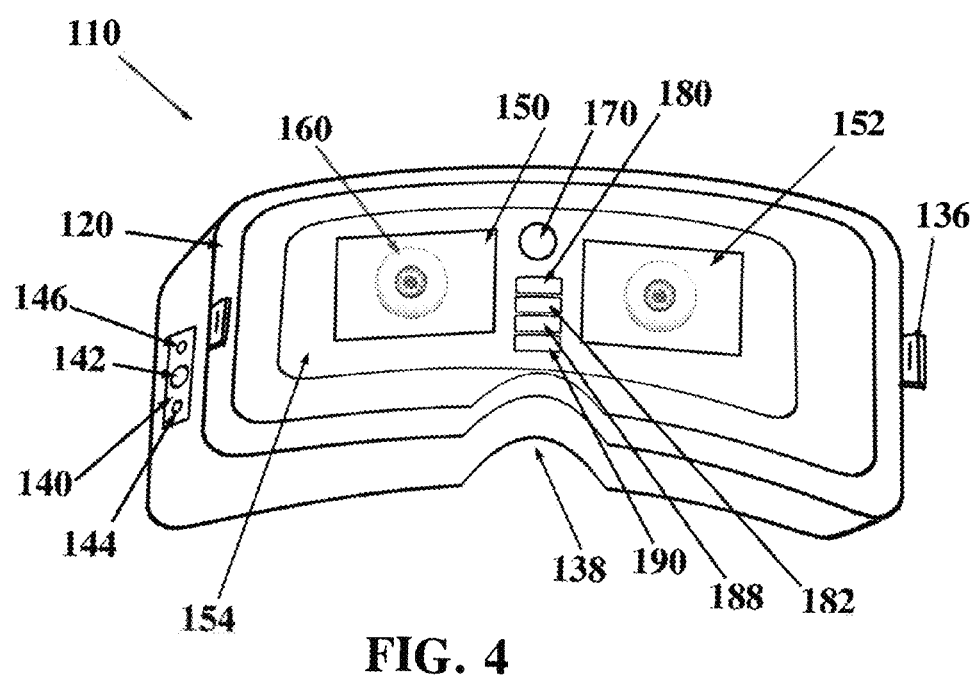
FIG. 4 is a rear left bottom perspective view of the physician headset shown in FIG. 3.

One embodiment of the present invention is shown in FIGS. 1-4. The patient headset 10 is shown in FIGS. 1 and 2 while FIGS. 3 and 4 show the physician headset 110. The patient headset 10 is the source of the patient biomedical digital camera data that is used by the physician to screen the patient organs and glands for tumor biomarkers. The patient headset 10 includes a headset housing 20 having a housing shell 22 and includes finger slots 34 allowing ample room for the male or female patient to comfortably manipulate the eyelid, to remove unnecessary video noise such as eyelids, eyelashes, etc. The finger slots 34 may be disposed on any portion of the headset system housing shell 22. A microphone 35 may be disposed on the patient headset 10 for allowing audio input to the headset system. Although the microphone 35 is shown on the bottom portion of the shell housing, the microphone 35 may be disposed anywhere on or attached to the patient headset 10. FIG. 1 shows the finger slots 34 at a housing bottom while FIG. 2 includes the finger slots at the top and side portions of the shell housing. The patient headset 10 includes a headset plate 30 having a plate perimeter, a headset plate exterior surface and a headset plate interior surface 32. The headset plate 30 is secured to the housing shell 22 along the plate perimeter. The patient headset 10 includes a headset securing bracket 36 for engaging a securing device for donning the patient headset during the sclera exam. The patient headset includes a bilateral digital camera system, namely a left camera 50 and a right camera as depicted 52. The patient headset 10 includes a patient headset power source 70, a video processing system 80, a receiving/transmission communication system 82 and a CPU 88 for processing information in the headset. The patient headset 10 includes a memory storage drive 90, a circuit board 32 for integrating power source 70, video processing system 80, receiving/transmission communication system circuit 82, left camera 50, right camera 52, CPU 88 and memory storage 90. The patient may control the functions of the patient headset 10 with the control panel 40 having a combination of buttons 42, 44, and 46 which may include any hardware attachments suitable for the function like a wireless mouse, wireless keyboard, or any material technology known by one skilled in the art for input functionality. A map template database may be disposed in the memory storage 90 or in a physician headset in wireless communication with the patient headset 10. The map template database includes data specifying anatomical location of a patient tumor using sclera scans of a patient sclera and iris. The video processing system can capture high resolution images from the left camera and the right camera and integrate with a map template system for use by a medical doctor, chiropractor, naturopathic doctor, etc. Captured video information on the patient pupil, iris, and sclera is saved in the memory storage drive, labeled by the physician, and stored securely, and provided in a format to match with the map template system in the physician headset. The power source may include a rechargeable battery such as graphene technology, and the housing shell may include a charging port to charge the rechargeable battery, or otherwise wireless charging functionality such as via a wireless charging pad.

FIGS. 3 and 4 show a physician headset 110 for wearable biomedical imaging functionality for early tumor detection. The physician headset 110 including a headset housing having a housing shell 122 including a nose rest 138, a headset plate (or visor) having a plate perimeter, the headset plate including a headset plate exterior surface 130 and a headset plate interior surface, the headset plate being secured to the housing shell 122 along the plate perimeter and a headset securing bracket 136 for engaging a securing device or "halo" for securing the physician headset 110. A microphone 135 may be disposed on the physician headset 110 for allowing audio input to the headset system. Although the microphone 135 is shown on the bottom portion of the shell housing, the microphone 135 may be disposed anywhere on or attached to the physician headset 110. The physician headset 110 includes a power source 170, a graphics processing system 180, a receiving/transmission communication system 182 for receiving and sending information to a patient headset and a CPU 188 for processing information in the headset. The physician headset includes a memory storage drive 190, a circuit board for integrating the power source 170, the graphics processing system 180, the receiving/transmission communication system 182, the CPU 188 and the memory storage drive 190 and at least one graphical display disposed on the interior surface of the headset plate, at least one graphical display for displaying sclera and iris scans received from a patient headset and overlaid template information based on the iris map and sclera map. The physician may control the functions of the physician headset 110 with the control panel 140 having a combination of buttons 140, 142, 144, 146 which may include wireless mouse, wireless keyboard, joysticks, momentary contact buttons, on/off buttons, or any other type which allows user input. The physician headset includes a map template database disposed in the memory storage drive wherein the map template database includes data specifying anatomical location of a patient tumor using sclera scans of a patient sclera and iris received from the patient headset; and a headset controller panel for controlling functions carried out by the headset. The graphics processing system processes high-resolution images of the patient's eye culled from the patient headset, usually about twelve total digital images per eye, or twenty-four total pictures for both eyes, and display the high-resolution photos in combination with the corresponding iris and sclera template data for review by a physician. The medical doctor, chiropractic doctor, or naturopathic doctor, can don the physician headset at 110, access the sclera scans from the patient headset software system, and the map template database data from the memory storage drive. Captured video patient biodata of the pupil, iris, and sclera, is securely saved in the memory storage drive, labeled by the physician, securely stored in compliance with HIPPA, and provided in a format to match with the iris and sclera map template system. The map template database may be comprised of both a Physical Iridology and a Sclerology map template database. The headset controller panel may be remote and in wireless communication with the receiving/transmission communication system. The at least one graphical display may be mounted on the circuit board. The power source may include a rechargeable battery, and the housing shell may include a charging port to charge the rechargeable battery, or else wireless charging functionality; one skilled in the art would know best what battery technology is appropriate. The physician headset may include wireless communication functionality allowing the doctor to communicate freely with the patient over any geographic distance. The physician headset may operate independent of a PC, laptop, and cellphone or tablet. Communication through physician headset may be secured for HIPAA or other policy compliance. Both the physician and the patient headset will feature secured biometric iris scan access to ensure confidentiality of medical records under HIPAA. The physician headset may include AI/ML functionality and a supervised algorithm. The supervised algorithm will be fed an initial dataset, and this will be used to train the algorithm over time. The learning algorithm will then examine each patient anterior segment (pupil border dynamics, iris markers, and N12 and D5 scleral tumor markers) against the exemplars in the dataset to help predict the statistical probability output of genetic predisposition to future tumor formation. The utility of the algorithm is to benefit society at large, by reducing the appalling rate of cancer misdiagnosis by way of false positives and false negatives from human physicians. Another aspect of the present invention is directed to an independent wearable biomedical imaging system for early tumor detection the system comprising a physician headset 110 having a headset housing 130 having a housing shell 122 including a nose rest 138, a headset plate 130 (or visor) having a plate perimeter, the headset plate 130 including a headset plate exterior surface and a headset plate interior surface, the headset plate 130 being secured to the housing shell 122 along the plate perimeter. The physician headset 110 includes a headset securing bracket 136 for engaging a securing device for donning the physician headset comprised of a natural and robust material. The securing device may be a strap or a hard frame or "halo" ideally made of natural material suitable for securing the patient headset securely to the patient's head for maximum comfort for the user. The physician headset 110 includes a power source 170, a graphics processing system 180, a receiving/transmission communication system 182 for receiving and sending information to a patient headset and a CPU FIG. 4 188 for processing information in the physician headset. The physician headset 110 includes a memory storage drive 190, a circuit board 154 for integrating the power source 170, the graphics processing system 180, the receiving/transmission communication system 182, the CPU 188 and the memory storage drive 190 and at least one graphical display 150, 152 disposed on the interior surface of the headset plate 130, the at least one graphical display 150, and 152 for displaying patient sclera and iris scans received from a patient headset and overlaid template information iris and sclera maps 6 and 8 and 9 respectively. The physician may control the functions of the physician headset with the control panel 140 having a combination of buttons 142, 144, 146 which may include wireless mouse, wireless keyboard, joysticks, momentary contact buttons, on/off buttons, or any other type which allows user input as best determined by one skilled in the art. The physician headset includes a map template database disposed in the memory storage drive 190 wherein the map template database includes data specifying anatomical location of a patient tumor using sclera scans of a patient sclera and iris received from the patient headset; and a headset controller panel for controlling functions carried out by the headset. The graphics processing system 180 processes high-resolution digital images of the patient biodata from the patient headset, and can display the high-resolution image data in combination with corresponding template data for review by a physician. The physician can don the physician headset, visually access the sclera scans from the patient headset and the map template database data from the memory storage drive 190. Captured video information of the patient pupil, iris, and sclera, is saved in the memory storage drive, labeled by the physician, and stored securely to protect patient medical records confidentiality in compliance with the HIPAA. The patient biodata is provided in a format to match with the map template system. There are ample finger slots on the patient headset 34 for the patient to comfortably insert fingers to lift up on the eyelid, pull down on the eye lid, pull laterally on the eyelid, in order to remove unwanted noise from the digital camera system that are disposed in the patient headset housing 22. The patient headset includes a cavity containing a left camera 50, a right camera 52, a battery 70, a video processing system 80, a receiving/transmission circuit 82 and a patient headset CPU 88 for controlling the patient headset, and a small fan or other cooling system to keep the electronics from overheating and causing discomfort for the user. The video processing system captures high resolution images from the left camera 50 and the right camera 52 and integrates with the iris and sclera map template. With each sclera exam, a supervised learning algorithm may learn to feature recognize and feature extract the pupil, iris, and sclera tumor biomarkers that indicate genotype predisposition to tumors based on the science of Physical Iridology, as well as "real time" early tumor formation in the patient organs and glands using the gold-standard N12 and D5 histopathological tumor biomarkers. The algorithm would amass an ever-increasing quantity of patient digital imagery biodata upon each patient sclera exam, whereupon it could surpass even the most experienced human Sclerologist in feature recognition and feature extraction of tumor biomarkers. The algorithm would ideally be utilized to help the chiropractor, naturopathic doctor, and medical doctor, generate accurate sclera reports on statistical probability of genetic predisposition to cancer, as well as evidence of "real time" cancer formation, with minimal errors that typically accompany patient cancer detection by doctors alone.

Figure 5:
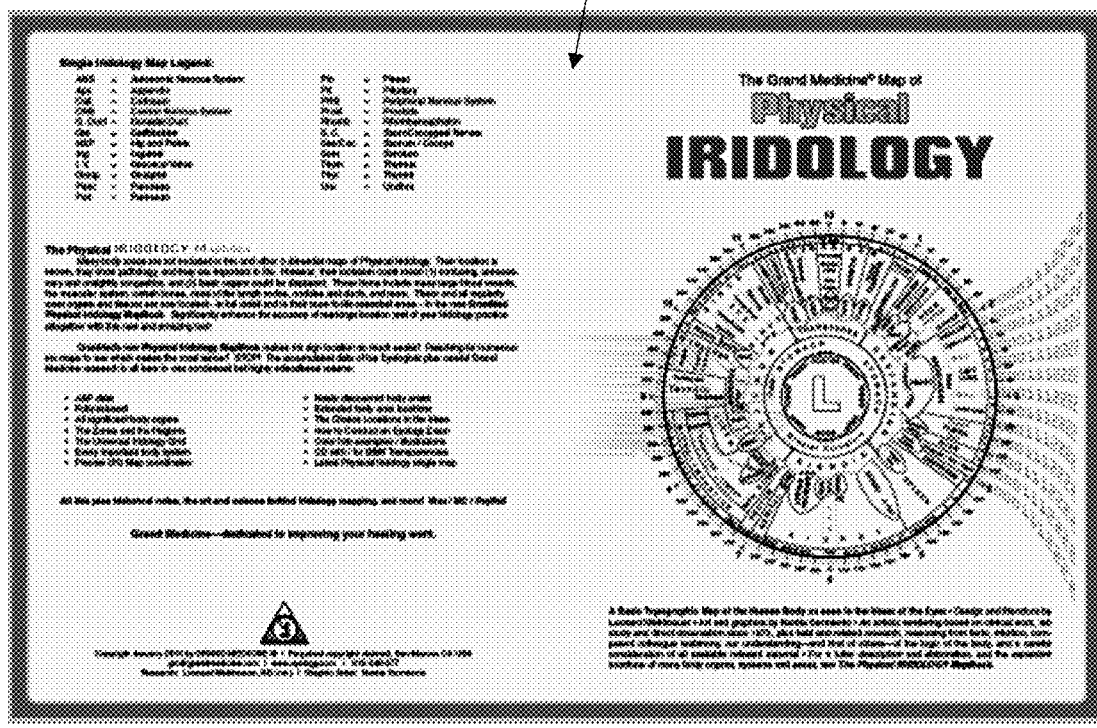
FIG. 5 shows a front page of an exemplar Physical Iridology map for illustrative purposes.
Figure 6:
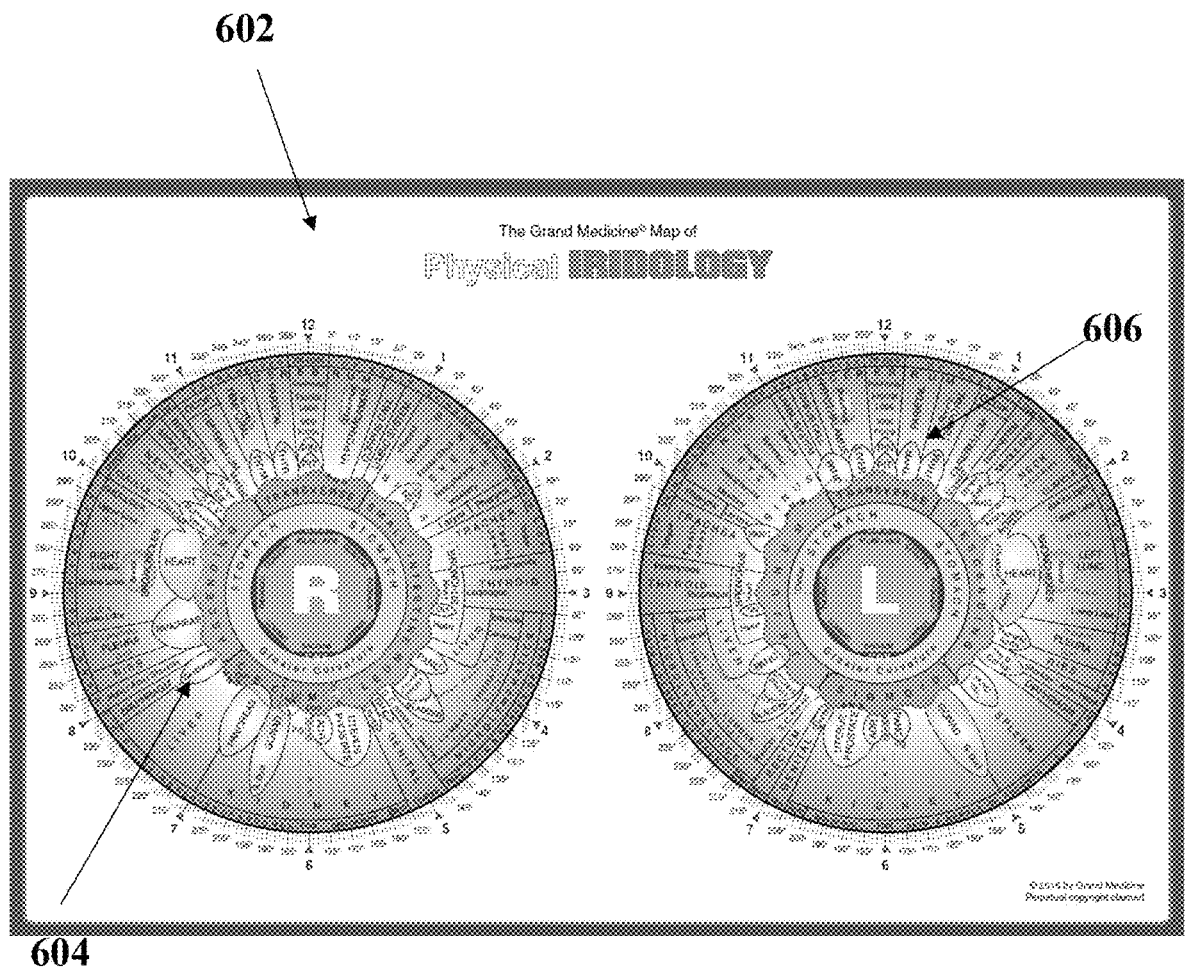
FIG. 6 shows a second page of the Physical Iridology map shown in FIG. 5 as an exemplar for illustrative purposes.
Figure 7:
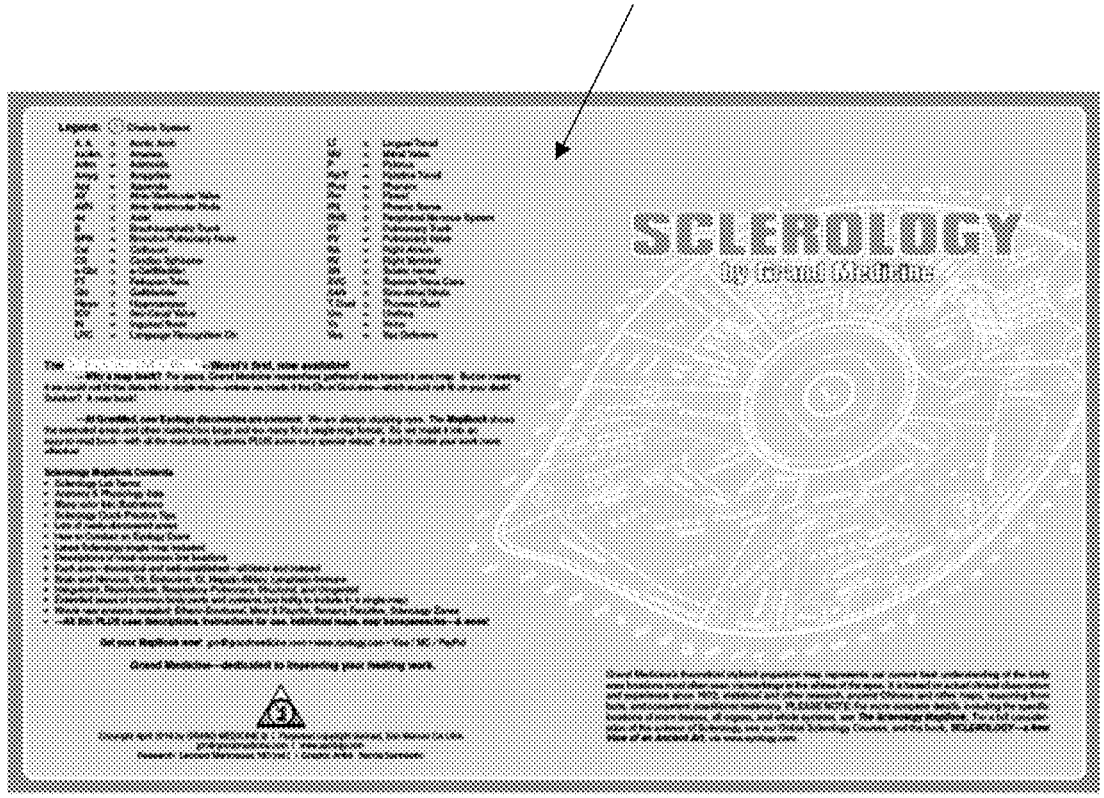
FIG. 7 shows a front page of a Sclerology map as an exemplar for illustrative purposes.
Figure 8:
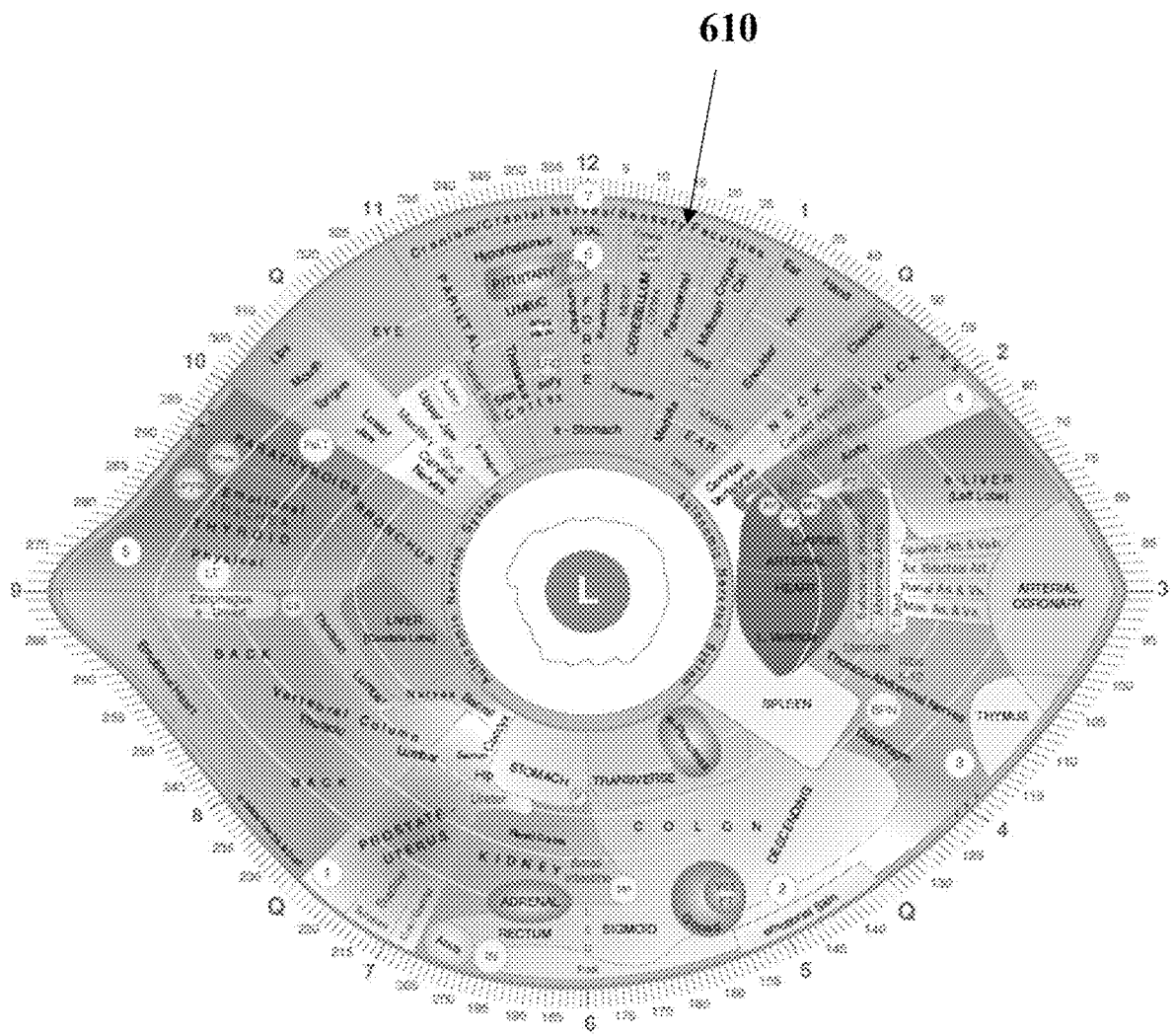
FIG. 8 shows an illustration of a left eye of the Sclerology map shown in FIG. 7 as an exemplar for illustrative purposes.
Figure 9:
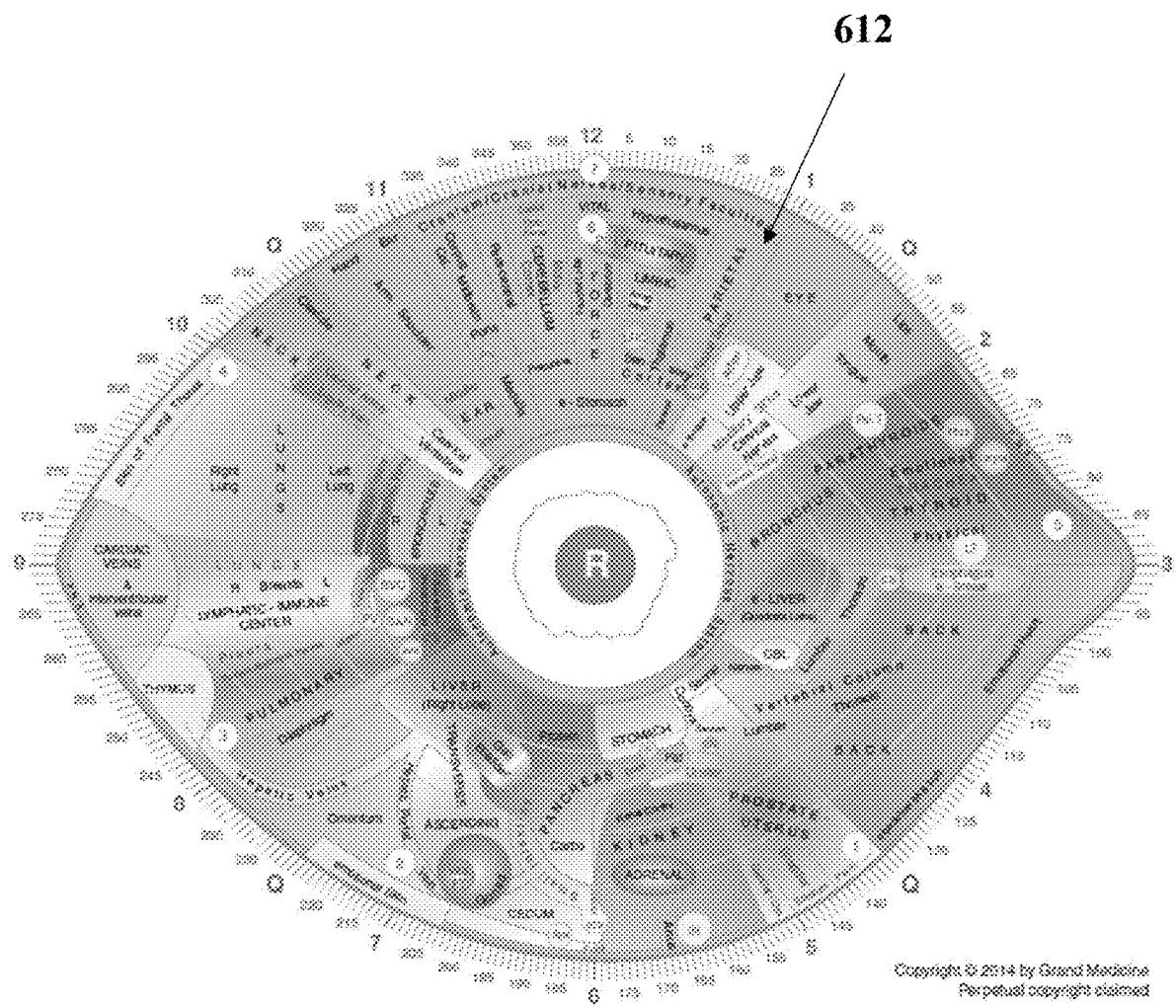
FIG. 9 shows an illustration of a right eye of the Sclerology map shown in FIG. 7 as an exemplar for illustrative purposes.

FIG. 5 shows an exemplar Physical Iridology map 600 including a chart 602 presenting bi-laterally each eye of the patient FIG. 6, and the corresponding zone of each internal bodily organ and gland location 604, 606. FIG. 7 shows the exemplar Sclerology map by Grand Medicine 608. FIG. 8 depicts an exemplar of the type of template that would be available in the physician headset 610. FIG. 9 depicts the right sclera map that will be used in the physician headset as a reference for each patient examination 612.

Figure 10:
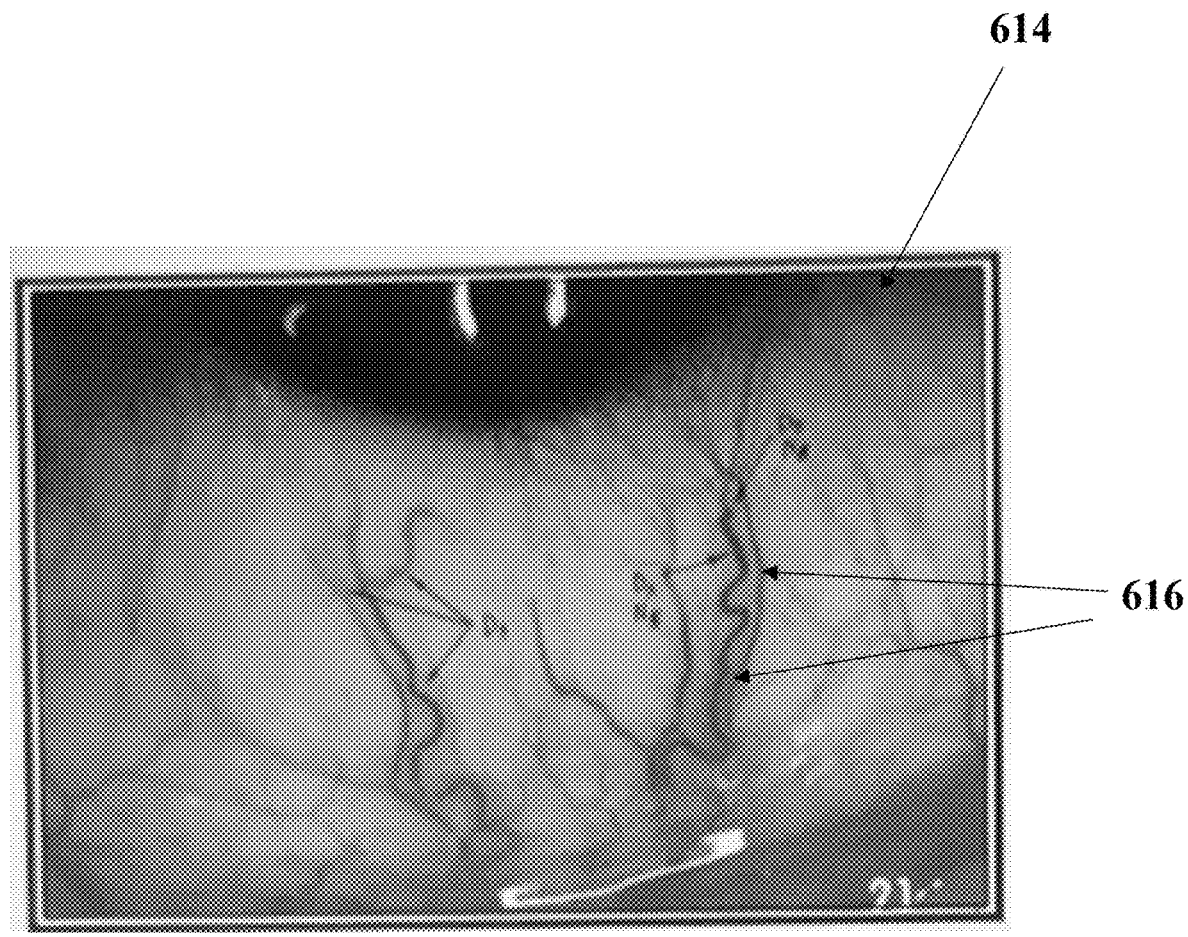
FIG. 10 is a digital photo of a patient lower sclera depicting exemplar D5 tumor biomarkers for illustrative purposes.

The FIG. 10 slide 614 shows an exemplar patient sclera lower quadrant depicting tumor biomarkers 616.

Figure 11:
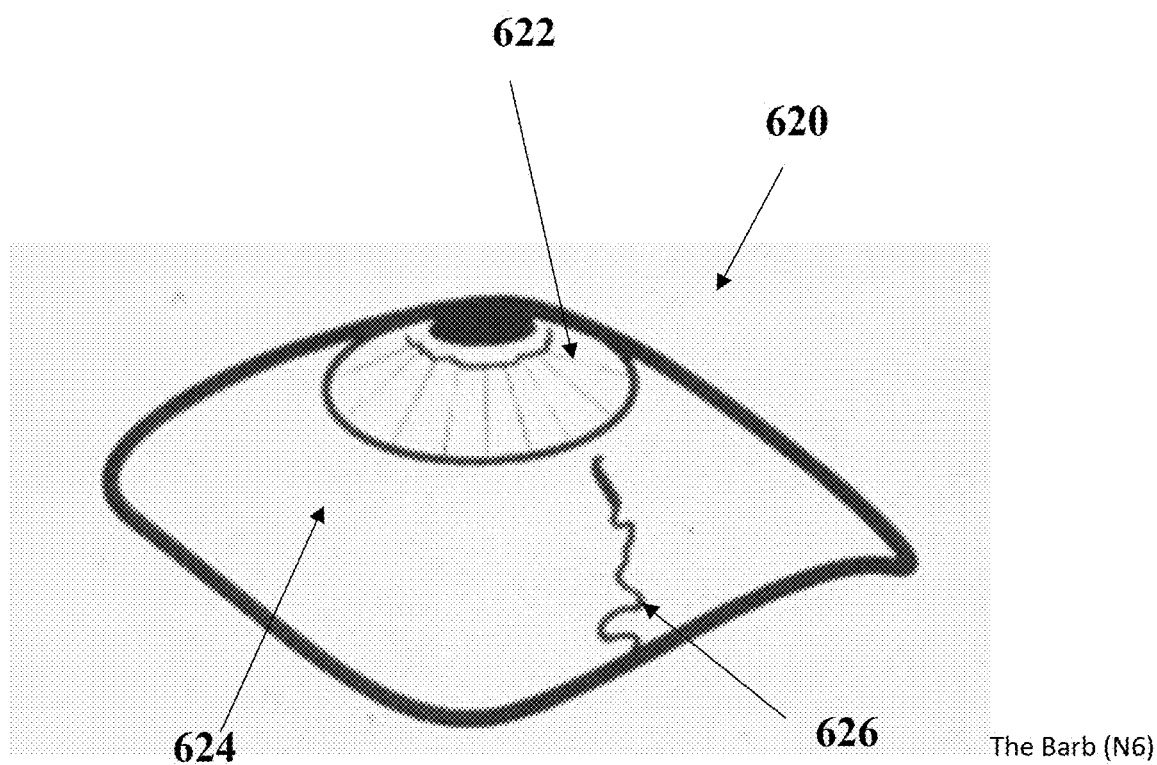
FIG. 11 is a line drawing of a patient lower right quadrant of the sclera depicting the N6 neoplasm tumor biomarker.

The FIG. 11 eye drawing 620 depicts a clinical drawing of a patient exhibiting the N6 scleral tumor biomarker 626 in the right lower quadrant of the sclera 624. Iris 622 is also shown.

Figure 12:
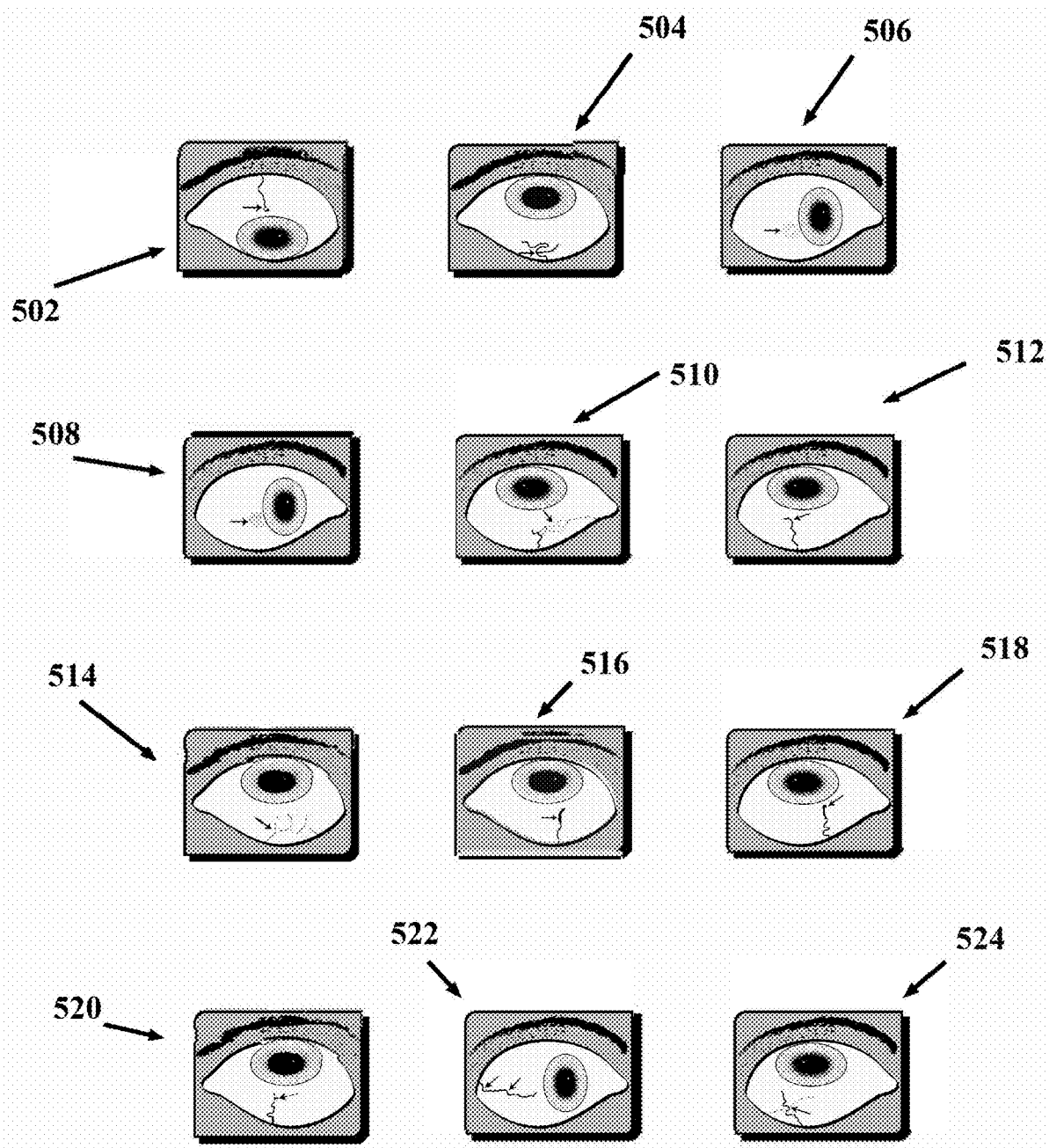
FIG. 12 shows twelve histopathological tumor biomarkers based on Dr. Mehlmauer's pioneering research at Grand Medicine, these N12 tumor markers represent the gold-standard and will be used to train the supervised learning algorithm; the N12 tumor markers are provided for illustration.
Figure 14:
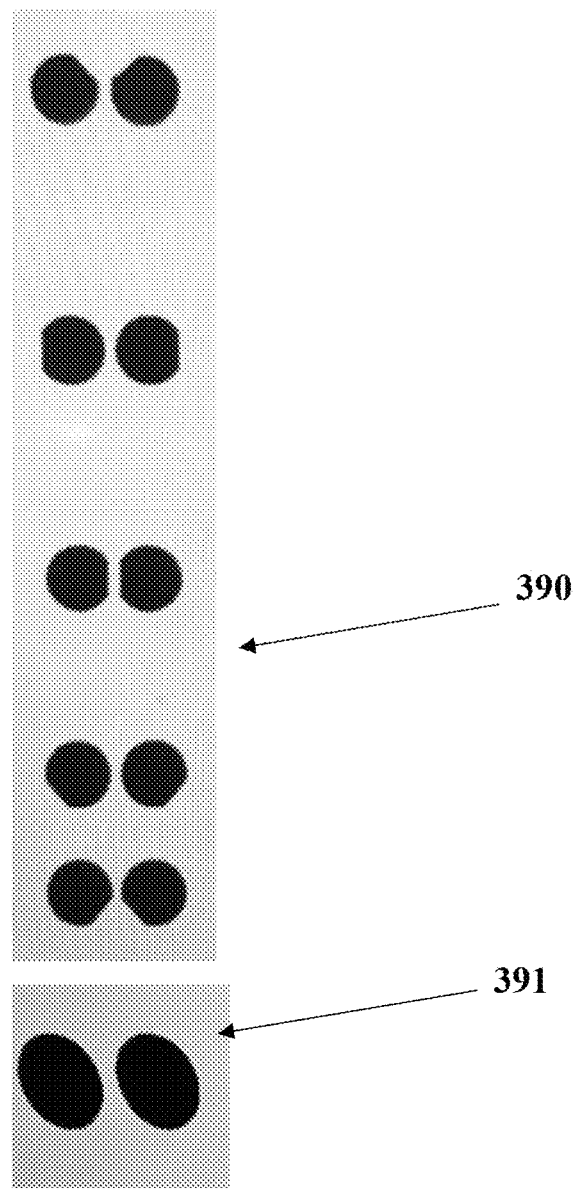
FIG. 14 is an exemplar for pupil tumor biomarkers, and will be used to train the algorithm; the pupil border dynamics chart is included herein for illustrative purposes.

FIG. 12 shows the exemplar histopathological N12 tumor biomarkers 502-524 (even) discovered by world leading Sclerologist Dr. Mehlmauer. These represent the gold-standard in tumor biomarkers that can show evidence of sub-clinical neoplasms in the body organs and glands "years before patient pain symptoms." The biomarkers shown in FIG. 12 are as follows:

Encapsulations in slide 502 show an enclosure of a potentially wide variety of materials, from fatty cells to parasites. The sign can indicate (and often does) benign circumstances. They can also be associated with malignancy (i.e., they can open, invade, and metastasize);

Perpendiculars in slide 504 show tumor development, which may be benign or malignant. A topostabile sign that may occur in any Quadrant. With this sign, there is a 97% chance of the tumor being benign;

Latent Neoplasm or Pale Fine Webbing in slide 506, this topolabile sign shows a significant potential for neoplastic tissue to develop. High emotional stress is frequently involved with the appearance of this sign;

N1 (n=neoplasm) in slide 508, Fine Webbing is the first clear sign that neoplasm is developing. Look for the fine-mesh webbing that is clearly etched. With other appropriate signs, symptoms and studies to confirm, active neoplasm is indicated. The presence of other "N" signs always helps confirm neoplasm activity, although malignancy can be shown by one marker only. The N1 is associated with mildew-type fungi;

N2 in slide 510, Large Webbing is signed by an enlarged version of the fine Webbing sign. The webbing may be quite large. This sign is most often seen in GI and Urogenital organ areas. Certain types of powerfully life-negative health-destroying bacteria are associated with this sign;

N3 in slide 512, Half Moon is a topolabile sign showing neoplasm presence as a crescent shaped portion of a line. The line will be moderate-to-heavy in thickness, and can appear within or at the end of a line. (Be careful in your observations: beginning students tend to find Half Moons and other "N" signs everywhere—even where they are not!) Flukes are often associated with this sign;

N4 in slide 514, the Bulwark is a neoplasm marker resembling the bulwark structure under bridges or otherwise in building construction. It is identified as usually medium to-thick branching straightish lines that seem to be connected-at-the-joints. They can be found in any quadrant. The N4 is topostabile, indicating that the lesion is located wherever the sign is found. Worms (P10) are often associated with this sign;

N5 in slide 516, the Thickening Line is identified by the unusual fact that, unlike most sclera lines (that are thickest at their base, and thin out as they approach the iris), it thickens as it approaches the iris. It is topostabile. Some very nasty bacteria (P4) are always associated with the N5;

N6 in slide 518, the Barb is a tiny marking on the end of a line, typically a Thickening Line (N5), indicating an active malignancy. This marking is topostabile. The line that it derives from will often show negative pathology that contributed to the development of the malignancy, like drug abuse or parasites, etc. Somehow, certain fungi (P5) are always found in situations where this sign is seen;

N7 in slide 520, the Stubby is another topolabile neoplasm marker. It seems always to be associated with mold-type fungi (P8). This sign, although smallish, is either moderately thick or very thick, and appears like a cut-off stubby branch of a tree, coming out at a right angle, perpendicular to the trunk;

N8 in slide 522, Right Angle is often a dramatic-appearing marker showing malignant neoplasm. It locates the lesion (topostabile). In identifying it, be sure the angle is clearly seen and not much rounded at all. Usually, with this sign, combinations of three different parasites are common, including bacteria and fungi; and N9 in slide 524, the Detour is a malignant neoplasm marker that resembles a wiring diagram sign. The lesion is not necessarily where this sign is seen (topolabile). Worms (P10), more than the other parasites, are most often associated with this sign;

D5, (d=drug) Drug-Induced Neoplasm is also a topostabile sign, in this case showing that drug was involved in the development of the neoplasm. Malignancy is indicated, and tests should be run if the disease has not yet been medically diagnosed. However, many medical tests are too gross to find some early-stage malignancies. Begin natural high-raw veggie diet and life-positive lifestyle immediately. The D5 tumor biomarker is not presented in the FIG. 12. The Pupil Border Dynamics are assessed for the following tumor biomarkers:

Ellipses. As shown in FIG. 14 in chart 391, Right Circulatory & Eliminative systems; smoke abuse; reflux; acidity; GI tumors. Circulatory and Eliminative systems. Electrolyte deficiency. Major mineral dysfunction/high tissue acidity. Low cardiac output. Pituitary lesions. Aldosterone dysfunction. Esophagus/upper stomach problems. Intestinal tumors . . . ;

Medial Flattening as shown in FIG. 14 chart 390. Heart, systemic vascular; stomach; connective tissue; vitamin metabolism. Bodily sensation. Heart, pulmonary, systemic vascular/blood: ischemia, stroke, tumor, infarct, arterio-/athero-sclerosis, neoplasm . . . .

Figure 18:
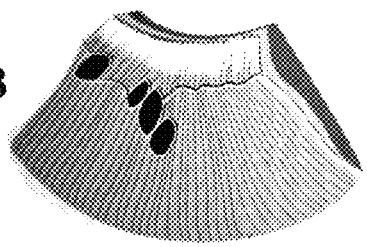
FIG. 18 shows a portion of an iris having Step Lacuna tumor biomarker.
Figure 19:
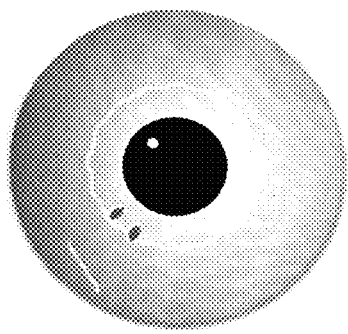
FIG. 19 shows a portion of an iris having Pancreatic Triad 2 tumor biomarker.
Figure 20:
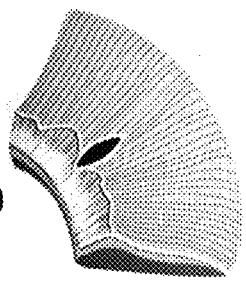
FIG. 20 shows a portion of an iris having Beak Lacuna tumor biomarker.
Figure 21:
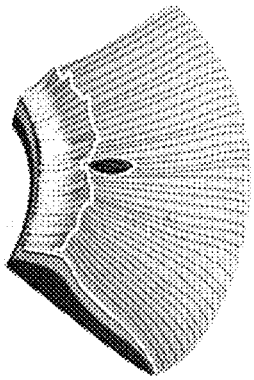
FIG. 21 shows a portion of an iris having Lance/Torpedo Lacuna biomarker.
Figure 22:
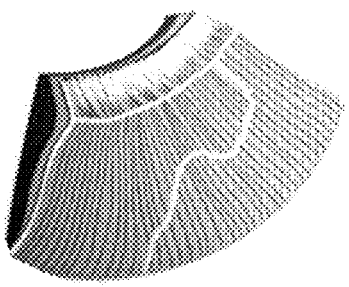
FIG. 22 shows a portion of an iris having Transversal biomarker.
Figure 23:
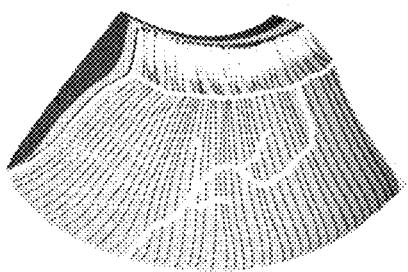
FIG. 23 shows a portion of an iris having Root Transversal tumor biomarker.
Figure 24:
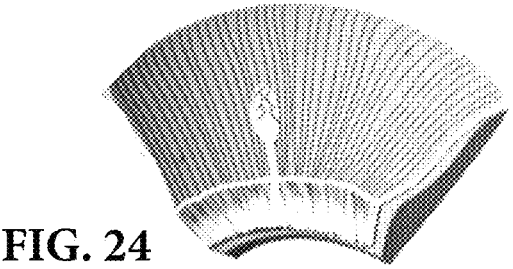
FIG. 24 shows a portion of an iris having Asparagus Transversal biomarker.

The iris tumor biomarkers are presented as follows: FIG. 18—Step Lacuna—Also called "Ladder", "Shingle", and "Stair-step" Lacuna, this marker has the appearance of steps in a stepladder, shingles on a roof, or stone steps in a garden. Most often seen attached to the Wreath, the sign indicates the possible development of cysts or tumors, which are somewhat more likely to be malignant than benign. Shown here is a potential brain area pathology;

FIG. 19—Pancreatic Triad 2—Predisposition to difficulties with gastric and pancreatic secretions, characterized by marked hypergastrinemia, gastric hyper-secretion, peptic ulceration, and diarrhea, caused by a gastrin-producing tumor (gastrinoma) of the pancreas or duodenal wall. The tumors may be single or multiple. Over ⅔ of the gastrinomas are malignant tumors and are commonly spread to the liver (shown by liver Transversal) and nearby lymph nodes. This disorder may occur at any age, but it is more likely to appear between 30 and 60, depending on the individual's lifestyle and emotional states. Possible symptoms are abdominal pain, diarrhea, internal bleeding, fatigue and weakness, yellow fat in the stool, and weight loss. (Use the sclera for differential Dx.);

FIG. 20—Beak Lacuna—This topostabile marker looks like the curved beak of certain birds. It is sometimes rounded on the outer end and but always pointed on the inner end (toward the Wreath). It suggests something a bit more (at least potentially) serious than the common Lacuna, such as a possible benign tumor formation. If a Beak Lacuna penetrates the Wreath, which it can do and sometimes does, there is much greater potential for harm, like bowel malignancy;

FIG. 21—Lance/Torpedo Lacuna—The "Lance" and "Torpedo" Lacunas have the same meaning. They just look a bit different. The Torpedo Lacuna is more rounded on both ends, while the Lance Lacuna is lance-like in appearance, with points at both ends. They tend to be seen in and around the R iris between 7:30 8:30Z3, involving the pylorus, duodenum, pancreas and gallbladder—although other locations are possible. They indicate potential abscess and tumor. As with other Hard Markers, they can show active pathology when Reflexers and Physiologics are present;

FIG. 22—Transversals and their Variants Transversals can be "vascularized", meaning taking on the appearance of blood vessels, with red inside. When red, they show actual blockage of blood vessels within local tissues. There is also a tendency for malignancy, tumor and other degenerative processes—especially when seen near other markings. In other words, Transversals seem to amplify the weakness or dysfunction when near other markings. They are a sign of at least potential significant irritation when seen alone. Other forms of transversals, besides the Red or Vascularized, include Root, Fork, and Rooftop;

FIG. 23—Root Transversal—This sign shows generally benign tumors, congestion, obstruction, inflammation and deformations. These are usually seen in the liver, spleen and gonad areas;

FIG. 24—Asparagus Lacuna—This unusual Lacuna, which looks like an asparagus tip, can occur anywhere, but most often is seen in the brain and genital areas. It suggests a tendency to various chronic, degenerative conditions, including (when in the brain) tumor. If you see one in brain areas, check for unusual symptoms such as dizziness, fainting spells, fluctuating blood pressure, and pressure on the ears. If tumor, the scleras should show the Straight Fork and very high congestion sign. If these appear along with symptoms, send the client in for MRI or CAT scan.

Each patient sclera exam will include system-wide non-invasive assessment of organs and glands, using the patient bilateral digital camera system in the patient headset 50, 52. FIG. 14 depicts the exemplar gold-standard reference for tumor biomarkers showing in the pupil. The utility of this particular chart is the medial flattening 390 can provide non-invasive evidence of tumor formation in the patient. Accordingly, the physician headset algorithm should also be trained with the gold-standard pupil border dynamics 390.

Figure 15:
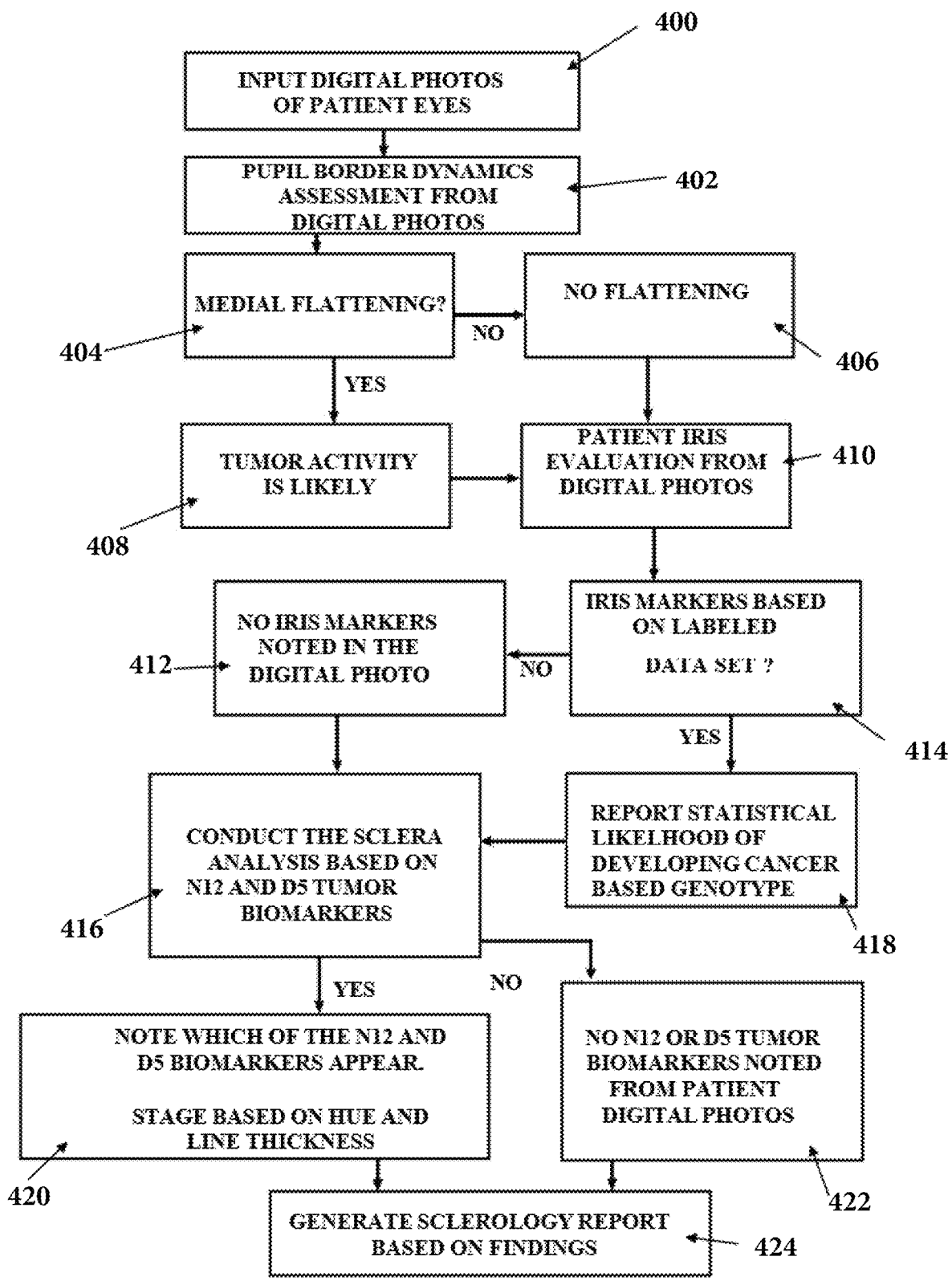
FIG. 15 is a flowchart showing the steps performed in a routine sclera exam for both the physician and the supervised learning algorithm.

FIG. 15 is a flowchart for illustrative purposes depicting the typical steps performed in the routine patient sclera exam for early cancer detection. This exam should only be performed by the chiropractor, naturopathic doctor, and medical doctor who is certified in the sciences of Physical Iridology and Sclerology. This exact same pathway will be used to label the datasets and train the supervised learning algorithm. The sequential steps of the examination include obtaining digital photos of the anterior segment of the patient pupil, iris, and sclera 400. Assessment of patient pupil border dynamics for established tumor biomarkers wherein the presence of tumor biomarkers will prompt a "yes" or "no" sequence 402. The next step involves examination of the patient iris for known tumor biomarkers suggesting genetic predisposition future pathology and actual tumor markers 410. If iris tumor biomarkers are detected based upon the labeled dataset both the human clinician, as well as the supervised learning algorithm 414 the next step is to generate a statistical probability of genotype vulnerability 418. If the human doctor and the learning algorithm determine that no iris tumor biomarkers are present 412 both the human physician and the algorithm move to the final stage 416. The final stage is to bilaterally assess each patient sclera quadrants for any of the thirteen N12 and D5 tumor biomarkers 416 (See FIG. 12 exemplars). If no scleral tumor biomarkers are detected, advance to 422. If any N12 or D5 tumor biomarkers are detected, 420. This concludes the routine sclera exam for cancer screening. The physician reviews the patient biodata, and prepares a sclera report based upon the findings 424. The physician may schedule a follow-up appointment with the patient to review the cancer screening findings 424.

Figure 16:
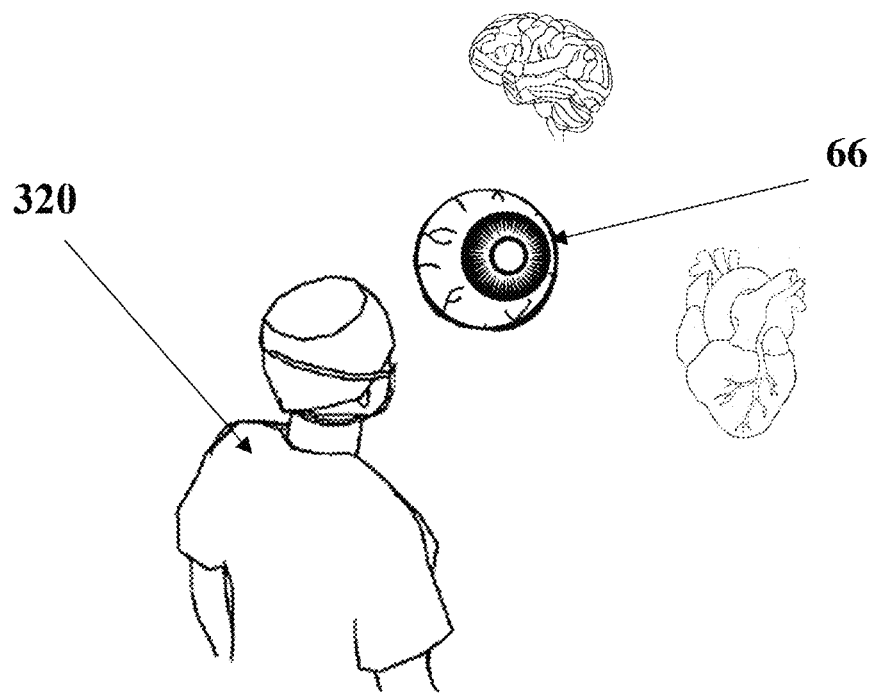
FIG. 16 shows a physician using holography for examining.

FIG. 16 shows a physician using medical holography, one of the features of some embodiments of the wearable technology, for examining actual patient images along the x, y, z axis of real space where a holographic image of an eye 66 or any other organ as shown in samples of the brain and heart, can be viewed by the physician 320 at any angle and manipulated by the physician 320.

Figure 17:
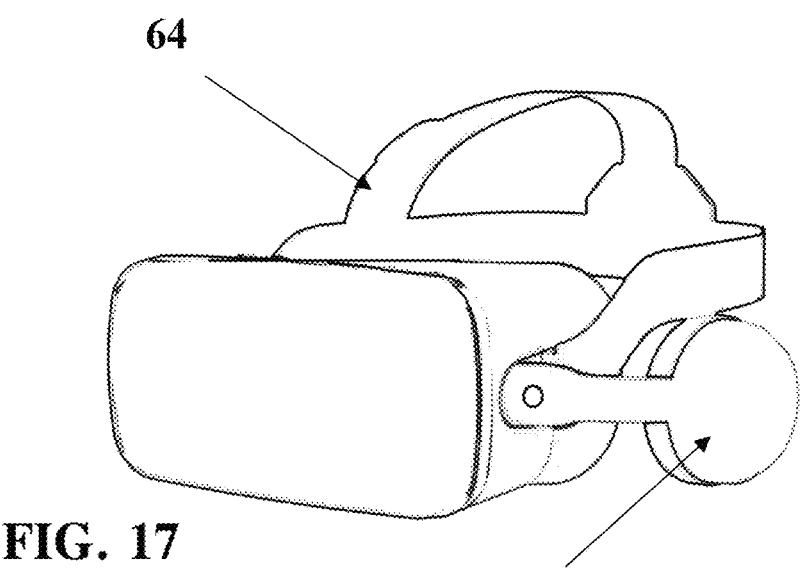
FIG. 17 shows a headset support and audio system included with a patient or physician headset.

FIG. 17 shows a complete headset exemplar with vertical cranium support 64 which may further secure the headset on a patient or physician. An "off ear" bilateral audio system 68 is disposed on the physician headset and patient headset, and may include earphones, earbuds or off-the-ear speakers for listening to the patient or physician, programming material, control material and the like, enabling effective and high-quality audio communication between the physician headset and the patient headset regardless of geographic distance. One of the headset controls 42, 44, 46, 142, 144, 146 may be used for control of audio input, audio output sound levels, and the like. There may be any number of headset controls (buttons, switches, joysticks, etc.) to allow for patient and physician control of the corresponding headset and communication between the patient headset and physician headset.

Figure 13:
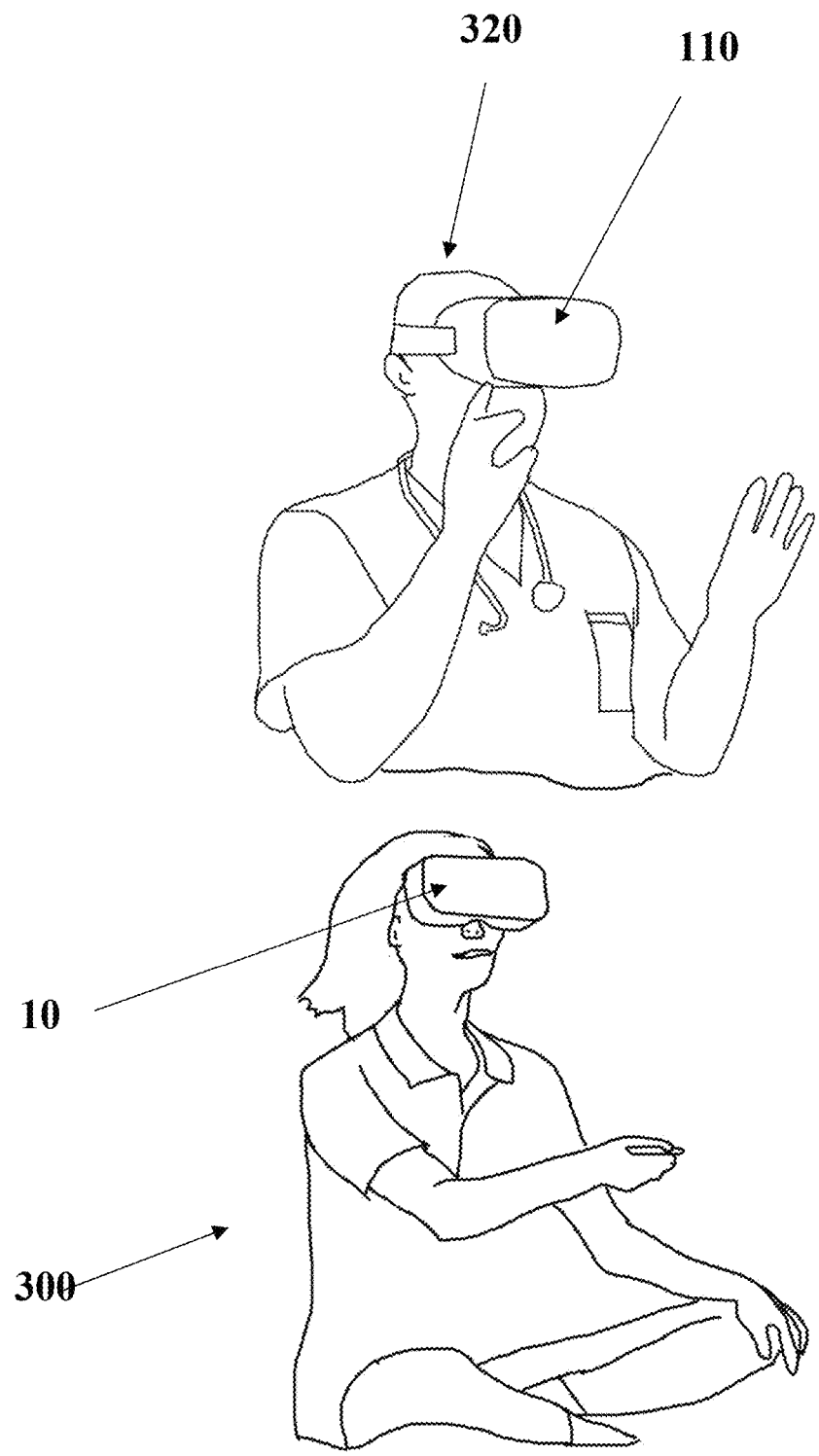
FIG. 13 shows a physician in one location and a patient in another location, the physician performs a remote and non-invasive sclera exam for cancer screening with the female patient.

FIG. 3-4 show a front and rear view of the physician headset 110. FIG. 13 shows a physician 320 wearing a stethoscope as well the physician headset 110 about to initiate a sclera exam with a patient three thousand miles away from the doctor in the comfort of her home 300. The typical sclera exam for early malignant tumor detection takes about ten minutes and would generally proceed as follows. The physician dons the physician headset 110 and initiates the examination using solely the headset technology untethered from a computer or laptop. Both the physician headset 110 and the patient headset 10 include secured biometric iris scan access for HIPAA compliance. With the use of voice command technology, wireless mouse, or wireless keyboard, the physician can access patient medical records and also patient digital image information from the patient headset. The physician headset also includes the most current Physical Iridology map (FIG. 6) and sclera maps (FIGS. 8 and 9) as templates which can be superimposed over the patient images in the headset to increase accuracy in anatomically placing the correct location of the tumor in the organs and glands; this having utility by helping mitigate medical misdiagnosis by the physician. The physician 320 may access the map data template on the graphical display 150, 152 of the physician headset. The physician 320 reviews the patient image information and the physician may then select an appropriate iris or sclera template based on examination findings. The method includes the physician 320 overlaying the patient's digital iris and sclera biodata from the sclera exam with the chosen template and comparing patient information against established gold-standard tumor biomarkers in the labelled dataset. The physician 320, having captured the patient digital imagery biodata, may use the wireless keyboard or wireless mouse to label the patient pictures in the medical records file stored in the software, and securely save the patient biodata (cloud) for later retrieval of the data for analysis. The algorithm continues to amass more and more learning experience with each sclera exam, until it amasses a sufficient database (hundreds of cancer patient exams) to soon outperform any human chiropractor, naturopathic doctor, and medical doctor in speed and accuracy of digital pathomics to determine statistical probability of cancer.

These and other objects, features, and advantages of the present invention will become more readily apparent from the attached drawings and the detailed description of the preferred embodiments, which follow.

In some embodiments the method or methods described above may be executed or carried out by a wearable untethered computing system including a tangible computer-readable storage medium, also described herein as a storage machine, that holds machine-readable instructions executable by a logic machine (i.e., a processor or programmable control device) to provide, implement, perform, and/or enact the above-described methods, processes and/or tasks. When such methods and processes are implemented, the state of the storage machine may be changed to hold different data. For example, the storage machine may include memory devices such as various hard disk drives, CD, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that a certain task is to be executed by the computing system, such as requesting the computing system to display any of the aforesaid information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API).

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

In addition, the present invention has been described with reference to embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

Insofar as the description above and the accompanying drawings disclose any additional subject matter that is not within the scope of the claims below, the inventions are not dedicated to the public and the right to file one or more applications to claim such additional inventions is reserved.

Although very narrow claims are presented herein, it should be recognized that the scope of this invention is much broader than presented by the claim. It is intended that broader claims will be submitted in an application that claims the benefit of priority from this application.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A physician headset for biomedical imaging for early tumor detection, the physician headset comprising:
   a headset housing having:
   a housing shell including a nose rest;
   a headset plate having a plate perimeter, the headset plate including a headset plate exterior surface and a headset plate interior surface, the headset plate being secured to the housing shell along the plate perimeter; and
   a headset securing bracket for engaging a securing device for donning the physician headset;
   a power source;
   a graphics processing system;
   a receiving/transmission communication system for receiving and sending information to a patient headset;
   a CPU for processing information in the physician headset;
   a memory storage drive;
   a circuit board for integrating the power source, the graphics processing system, the receiving/transmission communication system, the CPU and the memory storage drive;
   at least one graphical display disposed on the headset plate interior surface, the at least one graphical display for displaying sclera scans and iris scans received from the patient headset and overlaid template information;
   a map template database disposed in memory storage drive, wherein the map template database includes data specifying anatomical location of a patient tumor using the sclera scans and the iris scans received from the patient headset; and
   a headset controller panel for controlling functions carried out by the physician headset;
   wherein the graphics processing system processes image data from the patient headset and displays the image data in combination with corresponding template data for review by a physician;
   wherein the physician headset is configured to be donned by the physician wherein the sclera scans from the patient headset and the map template database data from the memory storage drive are visually accessed by the physician; and
   captured video information on the sclera, pupil and irises from the patient headset are saved in the memory storage drive, wherein the captured video information is labeled and stored securely, and provided in a format to match with the map template database.

2. The physician headset of claim 1 wherein the map template database is a Sclerology or Physical Iridology map template database.

3. The physician headset of claim 1 wherein the headset controller panel is remote and in wireless communication with the receiving/transmission communication system.

4. The physician headset of claim 1 wherein the at least one graphical display is mounted on the circuit board.

5. The physician headset of claim 1 where the power source includes a rechargeable battery and the housing shell includes a charging port to charge the rechargeable battery.

6. The physician headset according to claim 1 wherein the patient headset and the physician headset are configured to communicate wirelessly.

7. The physician headset according to claim 1 wherein the physician headset operates independent of a PC, laptop, cellphone or tablet.

8. The physician headset according to claim 1 wherein communication through the physician headset is secured through biometric iris scan access.

9. The physician headset according to claim 1, the physician headset is further configured to receive labelled datasets based on tumor biomarkers such that false positive or false negatives are reduced.

10. The physician headset according to claim 1, wherein the physician headset is further configured to display 3d holographic images.

11. A patient headset for biomedical imaging for early tumor detection, the patient headset comprising:
   a headset housing having:
   a housing shell including finger slots with sufficient space configured to allow a patient to digitally pull up, down, and laterally on the eyelid to remove noise artifacts including eyelashes or eyelids and to expose four or more quadrants of a sclera for high resolution digital photography;
   a headset plate having a plate perimeter, the headset plate including a headset plate exterior surface and a headset plate interior surface, the headset plate being secured to the housing shell along the plate perimeter; and
   a headset securing bracket for engaging a securing device for donning the patient headset;
   a left camera and a right camera;
   a patient headset power source;
   a video processing system;
   a receiving/transmission communication system;
   a CPU for processing information in the patient headset;
   a memory storage drive;
   a circuit board for integrating the patient headset power source, the video processing system, the receiving/transmission communication system circuit, the left camera, the right camera, the CPU and the memory storage drive; and
   a map template database disposed in the memory storage drive or in wireless communication with the patient headset;
   wherein the map template database includes data specifying anatomical location of a patient tumor using sclera scans and iris scan of the patent;
   wherein the video processing system captures high resolution images from the left camera and the right camera and integrates with a map template system for configured to be used by a physician; and captured video information on the patient pupil, iris, and sclera is saved in the memory storage drive, wherein the captured video information is labeled and stored securely, and is provided in a format to match with the map template system.

12. The patient headset of claim 11 where the patient headset power source includes a rechargeable battery and the housing shell includes a charging port to charge the rechargeable battery.

13. A wearable biomedical imaging system for early tumor detection, the system comprising:
- the physician headset according to claim 1;
- a patient headset including a patient headset housing having finger slots disposed in the patient headset housing, wherein the patient headset includes a cavity containing a left camera, a right camera, a battery, a video processing system,
- a patient receiving/transmission circuit, and
- a patient headset CPU for controlling the patient headset;
- wherein the video processing system captures images from the left camera and the right camera and integrates with the map template;
- wherein patient records from the patient headset are configured to be accessed by physician headset; and
- wherein the imaging system further performs capturing patient biodata, saving and labeling the pictures in medical records and securely storing the patient data for later retrieval of the patient biodata for analysis.

14. The wearable biomedical imaging system of claim 13 wherein the imaging system is configured to collect and extract the pupil, iris, and sclera tumor biomarkers and generate reports of statistical probability output of patient genetic predisposition to tumors.

15. The wearable biomedical imaging system of claim 14, wherein the biomedical imaging system is configured to generate reports of statistical probability for malignant or benign tumor based on the patient biodata.

16. The wearable biomedical imaging system of claim 13 wherein the communicating is through secured biometric iris scan access.

17. The wearable biomedical imaging system of claim 13, wherein the physician headset is configured to receive labelled datasets based on tumor biomarkers such that false positive or false negatives are reduced.

18. The wearable biomedical imaging system of claim 13 wherein the physician headset is further configured to display 3d holographic images.

19. A method of using a wearable biomedical imaging system for early tumor detection, the method comprising:
- providing the wearable biomedical imaging system according to claim 13;
- accessing patient image information from the patient headset;
- accessing the map template database data;
- choosing an iris or sclera template based on the patient information;
- overlaying a patient graphical information with the chosen iris or sclera template; and
- generating a Sclerology or sclera report based on the patient biodata.

20. The method of using a wearable biomedical imaging system for early tumor detection of claim 19, further comprising:
- capturing the patient digital imagery biodata, saving and labeling the digital images in the medical records,
- storing the patient digital biodata for subsequent retrieval for analysis, and
- generating reports of statistical probability for malignant or benign tumor based on the patient biodata.

* * * * *